US011891378B2

(12) United States Patent
Lee et al.

(10) Patent No.: US 11,891,378 B2
(45) Date of Patent: *Feb. 6, 2024

(54) SMALL MOLECULE MODULATORS OF PANTOTHENATE KINASES

(71) Applicants: ST. JUDE CHILDREN'S RESEARCH HOSPITAL, INC., Memphis, TN (US); COA THERAPEUTICS, INC., San Francisco, CA (US)

(72) Inventors: Richard E. Lee, Cordova, TN (US); Rajendra P. Tangallapally, Collierville, TN (US); Charles O. Rock, Bartlett, TN (US); Suzanne Jackowski, Bartlett, TN (US); Anne V. Edwards, Memphis, TN (US); Mi Kyung Yun, Collierville, TN (US); Chitra Subramanian, Cordova, TN (US); Robert Zamboni, Beaconsfield (CA); T. Jagadeeswar Reddy, Pierrefonds (CA)

(73) Assignees: ST. JUDE CHILDREN'S RESEARCH HOSPITAL, INC., Memphis, TN (US); COA THERAPEUTICS, INC., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/958,022

(22) PCT Filed: Dec. 26, 2018

(86) PCT No.: PCT/US2018/067539
§ 371 (c)(1),
(2) Date: Jun. 25, 2020

(87) PCT Pub. No.: WO2019/133635
PCT Pub. Date: Jul. 4, 2019

(65) Prior Publication Data
US 2021/0061788 A1   Mar. 4, 2021

Related U.S. Application Data

(60) Provisional application No. 62/610,835, filed on Dec. 27, 2017.

(51) Int. Cl.
*C07D 403/04*    (2006.01)
*A61K 31/197*    (2006.01)
(52) U.S. Cl.
CPC .......... *C07D 403/04* (2013.01); *A61K 31/197* (2013.01)
(58) Field of Classification Search
None
See application file for complete search history.

(56) References Cited

U.S. PATENT DOCUMENTS

| 7,754,724 | B2 | 7/2010 | Lorsbach et al. |
| 8,153,633 | B2 | 4/2012 | Austin et al. |
| 8,227,467 | B2 | 7/2012 | Kyle et al. |
| 8,975,398 | B2 | 3/2015 | Hansen et al. |
| 10,899,734 | B2 | 1/2021 | Sharma et al. |
| 2003/0114517 | A1 | 6/2003 | Greenlee et al. |
| 2006/0035884 | A1 | 2/2006 | Neitzel et al. |
| 2009/0306100 | A1 | 12/2009 | Barbosa et al. |
| 2010/0004254 | A1 | 1/2010 | Sun et al. |
| 2010/0041663 | A1 | 2/2010 | He et al. |
| 2010/0210594 | A1 | 8/2010 | Wagner et al. |
| 2011/0021530 | A1 | 1/2011 | Billich et al. |
| 2011/0053233 | A1 | 3/2011 | Brown et al. |
| 2013/0072497 | A1 | 3/2013 | Lorsbach et al. |
| 2013/0157330 | A1 | 6/2013 | Zhang et al. |
| 2014/0275095 | A1 | 9/2014 | Dvorak et al. |
| 2015/0284746 | A1 | 10/2015 | Zhang et al. |
| 2019/0300499 | A1 | 10/2019 | Sharma et al. |
| 2020/0330450 | A1 | 10/2020 | Smith et al. |
| 2021/0023081 | A1 | 1/2021 | Jackowski et al. |

FOREIGN PATENT DOCUMENTS

| WO | WO-2003105853 A1 | 12/2003 |
| WO | WO-2004011441 A1 | 2/2004 |
| WO | WO-2004058754 A1 | 7/2004 |
| WO | WO-2005011653 A2 | 2/2005 |
| WO | WO-2005056015 A1 | 6/2005 |

(Continued)

OTHER PUBLICATIONS

Pratini et al., Treatment of Classic Pantothenate Kinase-Associated Neurodegeneration (PKAN) with Deferiprone and Intrathecal Baclofen. American Journal of Physical Medicine & Rehabilitation, 2013, 98, 728-733.*
Schafer, S., Kolkhof, P. Failure is an option: learning from unsuccessful proof-of-concept trials. Drug Discovery Today. Nov. 2008, 13, 913-916.*
Horig, H., Pullman, W. From bench to clinic and back: Perspective on the 1st IQPC Translational Research conference. Journal of Translational Medicine. Dec. 2004, 2, 44.*
Chemical Abstract Registry No. 953135-76-7, indexed in the Registry File on STN CAS Online Nov. 13, 2007.*
Bennett et al., Cecil Textbook of Medicine, 1996, 20$^{th}$ Edition, vol. 1, 1004-1010.
CAS Registry No. 1183793-26-1, Entered STN Sep. 13, 2009.

(Continued)

*Primary Examiner* — Po-Chih Chen
(74) *Attorney, Agent, or Firm* — Mintz, Levin, Cohn, Ferris, Glovsky & Popeo, P.C.

(57) ABSTRACT

The present disclosure relates to chemical compounds that modulate pantothenate kinase (PanK) activity for the treatment of metabolic disorders (such as diabetes mellitus type II), neurologic disorders (such as pantothenate kinase-associated neurodegeneration), pharmaceutical compositions containing such compounds, and their use in treatment. This abstract is intended as a scanning tool for purposes of searching in the particular art and is not intended to be limiting of the present invention.

3 Claims, No Drawings

(56) References Cited

FOREIGN PATENT DOCUMENTS

| WO | WO-2009106991 A2 | 9/2009 |
|---|---|---|
| WO | WO-2010007120 A1 | 1/2010 |
| WO | WO-2013004642 A1 | 1/2013 |
| WO | WO-2016168619 A1 | 10/2016 |
| WO | WO-2017223474 A1 | 12/2017 |
| WO | WO-2019133632 A1 | 7/2019 |
| WO | WO-2019133634 A1 | 7/2019 |
| WO | WO-2019133635 A1 | 7/2019 |
| WO | WO-2022133034 A1 | 6/2022 |

OTHER PUBLICATIONS

Cohen et al., The development and therapeutic potential of protein kinase inhibitors, Current Opinion in Chemical Biology, 1999, vol. 3, pp. 459-465.
Dansie et al., Physiological roles of the pantothenate kinases, Biochem. Soc. Trans., 2014, 42:1033-1036.
Database Biosis, Accession No. PREV198631080811, 1986, Abstract.
Database Biosis, Accession No. PREV200100537451, Oct. 2001, Abstract.
Database Registry (STN) Registry No. 1954499-65-0, entered Jul. 18, 2016.
Database Registry (STN) Registry No. 1956298-43-3, entered Jul. 20, 2016.
Dermer et al., Bio/Technology, 1994, 12:320.
European Patent Office, Extended European Search Report for EP Application No. 17816310.1., dated Oct. 29, 2019, 9 pages.
European Patent Office, Extended European Search Report for EP Application No. 18894179.3, dated Jul. 19, 2021, 7 pages.
European Patent Office, Extended European Search Report for EP Application No. 18895007.5 dated Aug. 19, 2021, 9 pages.
Freshney, Culture of Animal Cells, A Manual of Basic Technique, Alan R. Liss, Inc., 1983, New York, pp. 1-4.
Garcia et al., Germline Deletion of Pantothenate Kinases 1 and 2 Reveals the Key Roles for CoA in Postnatal Metabolism, PLoS one, 2012, vol. 7, Issue 7: e40871, 13 pages.
International Preliminary Report on Patentability dated Dec. 25, 2018 by the International Searching Authority for International Application No. PCT/US2017/039037, 6 Pages.
International Search Report, dated Nov. 9, 2017 by the International Searching Authority for International Application No. PCT/US2017/039037, 4 Pages.
International Search Report, dated Mar. 21, 2019 by the International Searching Authority for International Application No. PCT/US2018/067536, 2 pages.
International Search Report, dated Mar. 27, 2019 by the International Searching Authority for International Application No. PCT/US2018/067538, 3 pages.
International Search Report, dated Mar. 27, 2019 by the International Searching Authority for International Application No. PCT/US2018/067539, 2 pages.
Jackowski et al., Regulation of Coenzyme A Biosynthesis, Journal of Bacteriology, Dec. 1981, vol. 148, N. 3, pp. 926-932.
Johnson et al., Mitochondrial Localization of Human PANK2 and Hypotheses of Secondary Iron Accumulation in Pantothenate Kinase-Associated Neurodegeneration, Ann. New York Academy of Sciences, 2004, 1012: 282-298.
Kotzbauer et al., Altered Neuronal Mitochondrial Coenzyme A Synthesis in Neurodegeneration with Brain Iron Accumulation Caused by Abnormal Processing, Stability, and Catalytic Activity of Mutant Pantothenate Kinase 2, Journal of Neuroscience, Jan. 19, 2005, vol. 25, No. 3, pp. 689-698.
Kuo et al., Deficiency of pantothenate kinase 2 (Pank2) in mice leads to retinal degeneration and azoospermia, Hum. Mol. Genet., Jan. 1, 2005, vol. 14, No. 1, pp. 49-57.
Leeson et al., The influence of drug-like concepts on decision-making in medicinal chemistry, Nature Review Drug Discovery, Nov. 2007, vol. 6, pp. 881-890.
Leonardi et al., Coenzyme A: back in action, Progress in Lipid Research, 2005, 44, pp. 125-153.
Leonardi et al., Localization and Regulation of Mouse Pantothenate Kinase 2, FEBS Lett., Oct. 2, 2007, vol. 581, pp. 4639-4644.
Leonardi et al., Pantothenate Kinase 1 is Required to Support the Metabolic Transition from the Fed to the Fasted State, PloS one, Jun. 14, 2010, vol. 5, Issue 6, el1107, 12 pages.
Leonardi et al., Pank1 Deletion in Leptin-deficient Mice Reduces Hyperglycaemia and Hyperinsulinaemia and Modifies Global Metabolism without Affecting Insulin Resistance, Diabetologia, Jul. 2014, vol. 57, pp. 1466-1475.
PUBCHEM Compound Summary for CID 110727414, 'AKOS027640281', U.S. National Library of Medicine, (2016), (https://pubchem.ncbi.nlm.nih.gov/compound/110727414); p. 3.
PUBCHEM Compound Summary For CID 121060331 deposited on Jun. 17, 2016, pp. 1-10. pg. 3.
PUBCHEM Compound Summary for CID 75373203 Create Date: Jul. 12, 2014 (Jul. 12, 2014) Date Accessed: Feb. 20, 2019, p. 4, compound listed.
PUBMED Compound Summary for CID 53621124, 'MolPort-020-021-215', U.S. National Library of Medicine, 2011, (https://pubchem.ncbi.nlm.nih.gov/compound/53621124); p. 3.
Rinaldo et al., Effect of treatment with glycine and L-carnitine in medium-chain acyl-coenzyme a dehydrogenase deficiency, Journal of Pediatrics, Mosby-Year Book, St. Louis, MO, Apr. 1, 1993, vol. 122, No. 4, pp. 580-584.
Rock et al., The murine pantothenate kinase (Pank1) gene encodes two differentially regulated pantothenate kinase isozymes, Gene, 2002, vol. 291, pp. 35-43.
Sabatti et al., Genome-wide association analysis of metabolic traits in a birth cohort from a founder population, Nature Genet., Jan. 2009, vol. 41, No. 1, pp. 35-46.
Sharma et al., A High-Throughput Screen Reveals New Small-Molecule Activators and Inhibitors of Pantothenate Kinases, Journal of Medicinal Chemistry, 2015, vol. 58, pp. 1563-1568.
Shultz, Setting expectations in molecular optimizations: Strengths and limitations of commonly used composite parameters. Bioorganic & Medicinal Chemistry Letters, 2013, vol. 23, pp. 5980-5991.
Tafesse et al., Synthesis and evaluation of pyridazinylpiperazines as vanilloid receptor 1 antagonists, Bioorganic & Medicinal Chemistry Letters, Nov. 15, 2004, vol. 14, pp. 5513-5519.
Zhang et al., Feedback Regulation of Murine Pantothenate Kinase 3 by Coenzyme A and Coenzyme A thioesters, The Journal of Biological Chemistry, Sep. 23, 2005, vol. 280, No. 1, pp. 32594-32601.
Zhang et al., Biochemical Properties of Human Pantothenate Kinase 2 Isoforms and Mutations Linked to Pantothenate Kinase-associated Neurodegeneration, The Journal of Biological Chemistry, Jan. 6, 2006, vol. 281, No. 1, pp. 107-114.
Zhou et al., A novel pantothenate kinase gene (PANK2) is defective in Hallervorden-Spatz syndrome, Nature Genetics, Aug. 2001, vol. 28, pp. 345-349.
Written Opinion, dated Nov. 9, 2017 by the International Searching Authority for International Application No. PCT/US2017/039037, 5 pages.
Written Opinion, dated Mar. 21, 2019 by the International Searching Authority for International Application No. PCT/US2018/067536, 3 pages.
Written Opinion, dated Mar. 27, 2019 by the International Searching Authority for International Application No. PCT/US2018/067538, 4 pages.
Written Opinion, dated Mar. 27, 2019 by the International Searching Authority for International Application No. PCT/US2018/067539, 5 pages.
International Search Report for International Application No. PCT/US20221/063717, dated May 12, 2022, 4 pages.
Mitchell et al., Hereditary and acquired diseases of acyl-coenzyme A metabolism, Molecular Genetics and Metabolism, 2008, vol. 94, pp. 415.
National Institute of Neurological Disorers and Stroke, Refsum Disease Information Page, https://www.ninds.nih.gov/Disorders/All-Disorders/Refsum-Disease-Information-Page), 2019 (year:2019), 4 pages.

(56) References Cited

OTHER PUBLICATIONS

Waack et al., L-Malate's Plasma and Excretion Profile in the Treatment of Moderate and Severe Hemmorrhagic Shock in Rats, BioMed Research International, 2016, vol. 2016, 9 pages.
Yang et al., Hereditary diseases of coenzyme A thioester metabolism, Biochemical Society Transactions, 2019, vol. 47, pp. 149-155.
Written Opinion for International Application No. PCT/US2021/063717, dated May 12, 2022, 6 pages.

* cited by examiner

SMALL MOLECULE MODULATORS OF PANTOTHENATE KINASES

CROSS-REFERENCE TO RELATED APPLICATIONS

This application is the U.S. National Stage Entry under § 371 of International Application No. PCT/US2018/067539, filed Dec. 26, 2018, which claims the benefit of U.S. Provisional Application No. 62/610,835, filed on Dec. 27, 2017, the contents of which is incorporated herein by reference in its entirety.

BACKGROUND

Pantothenate Kinase (PanK, EC 2.7.1.33) catalyzes the biochemical conversion of pantothenate (vitamin B5) to phosphopantothenate and thereby initiates the biosynthesis of coenzyme A (CoA). In most organisms the activities of the PanK enzymes regulate the CoA intracellular concentration (Leonardi et al. (2005) Prog. Lipid Res. 44: 125-153; Jackowski and Rock (1981) J. Bacteriol. 148: 926-932; Zano et al. (2015) Mol. Genet. Metab. 116:281-288). CoA is an essential cofactor that functions as a carboxylic acid substrate carrier in various synthetic and oxidative metabolic pathways, such as the tricarboxylic acid cycle, sterol biosynthesis, heme biosynthesis, fatty acid and complex lipid synthesis and metabolism, and epigenetic modification of chromatin. Four closely related active PanK isoforms are identified in mammals: PanK1α, PanK1β, PanK2, and PanK3, which are encoded by three genes (Zhou et al. (2001) Nat. Genet. 28: 345-349; Zhang et al. (2005) J. Biol. Chem. 280: 32594-32601; Rock et al. (2002) Gene 291: 35-43). The PanKs regulate cellular CoA through feedback inhibition of the enzyme activity by CoA or CoA thioesters and each isoform responds to inhibition with a different sensitivity (Leonardi et al. (2005) Prog. Lipid Res. 44: 125-153). The PanK isoform expression profiles differ among individual cell types, tissues and organs and the relative abundance of one or more isoforms determines the respective CoA levels (Dansie et al. (2014) Biochem. Soc. Trans. 42:1033-1036).

Mutations in the human PANK2 gene result in a rare and life-threatening neurological disorder known as PanK-associated neurodegeneration (PKAN) (Zhou et al. (2001) Nat. Genet. 28: 345-349; Johnson et al. (2004) Ann. N. Y. Acad. Sci. 1012: 282-298; Kotzbauer et al. (2005) J. Neurosci. 25: 689-698). PKAN is an inherited autosomal recessive disorder that leads to progressive dystonia, dysarthria, parkinsonism, and pigmentary retinopathy. Classic PKAN develops in the first 10 years of life, starting around age 3; and patients are at risk for early death. The PANK2 gene is highly expressed in human neuronal tissues and many of the mutations associated with PKAN result in truncated or inactivated PanK2 protein expression, or severely reduced activity (Zhang et al. (2006) J. Biol. Chem. 281:107-114). The PANK2 mutations are predicted to result in significantly lower CoA levels, thereby reducing neuronal metabolism and function in PKAN patients. Tools are lacking for investigation of the relationship(s) between CoA levels and neurodegeneration. Activation of the PanK1 or PanK3 proteins that are also expressed in neuronal tissues (Leonardi et al. (2007) FEBS Lett. 581:4639-4644) could compensate for the reduction in PanK2 activity because functional redundancy among the isoforms is demonstrated in the Pank1$^{-/-}$ and Pank2$^{-/-}$ mouse models (Leonardi et al. (2010).

Limitation of the CoA supply by genetic deletion of Pank1 in mice blunts the increase in hepatic CoA in response to fasting. This, in turn, decreases fatty acid oxidation and glucose production by the liver resulting in fasting hypoglycemia (Leonardi et al. (2010) PloS one 5: e11107). Hypoglycemia and a significant reduction in fatty acid and ketone oxidation are the main causes for the early death of the Pank1$^{-/-}$ Pank2$^{-/-}$ mice in which both genes are deleted (Garcia et al. (2012) PLoS one 7: e40871). The ob/ob leptin-deficient mouse is a model of obesity-associated type II diabetes that exhibits abnormally high hepatic CoA (Leonardi et al. (2014) Diabetologia 57: 1466-1475). Consistent with the connection between hepatic CoA levels and glucose homeostasis, deletion of Pank1 in the ob/ob mouse reduces hepatic CoA and results in normalization of the diabetic hyperglycemia and associated hyperinsulinemia characteristic of this strain (Leonardi et al. (2014) Diabetologia 57: 1466-1475). A genome-wide association study (Sabatti et al. (2009) Nature Genet. 41: 35-46) indicates a significant correlation between PANK1 gene variants and insulin levels in humans, supporting the concept that PanK inhibitors may be useful therapeutics for diabetes. Taken together, these data demonstrate the impact of altering the intracellular level of CoA on oxidative metabolism and glucose homeostasis.

The associations of PanK with diseases like PKAN and diabetes led us to identify and develop PanK activators and inhibitors capable of modulating CoA levels and to assess the feasibility of such compounds as therapeutics in these diseases. We recently disclosed our initial high throughput screening effort towards this goal (Sharma et. al. (2015) J. Med. Chem. 58: 1563-1568). Our subsequent re-examination, careful filteration of hits and medicinal chemistry efforts identified new chemotypes capable of modulating PanK activity.

Despite the documented association of PanK with diseases like PKAN and diabetes, the feasibility of PanK antagonists capable of modulating CoA levels as disease therapeutics is uncertain. Thus, there remains a need for potent modulators of PanK to investigate the role of CoA in disease. The following disclosure describes a group of such compounds, as well as methods for making and using them.

SUMMARY

In accordance with the purpose(s) of the invention, as embodied and broadly described herein, the invention, in one aspect, relates to compositions and methods for use in the prevention and treatment of disorders associated with pantothenate kinase activity such as, for example, PKAN and diabetes.

Disclosed are compounds having a structure represented by a formula:

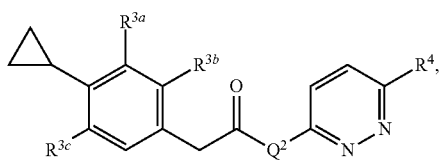

wherein $Q^2$ is a structure selected from:

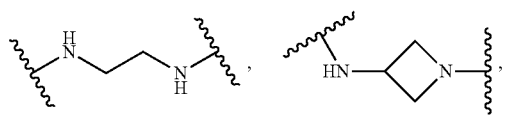

-continued

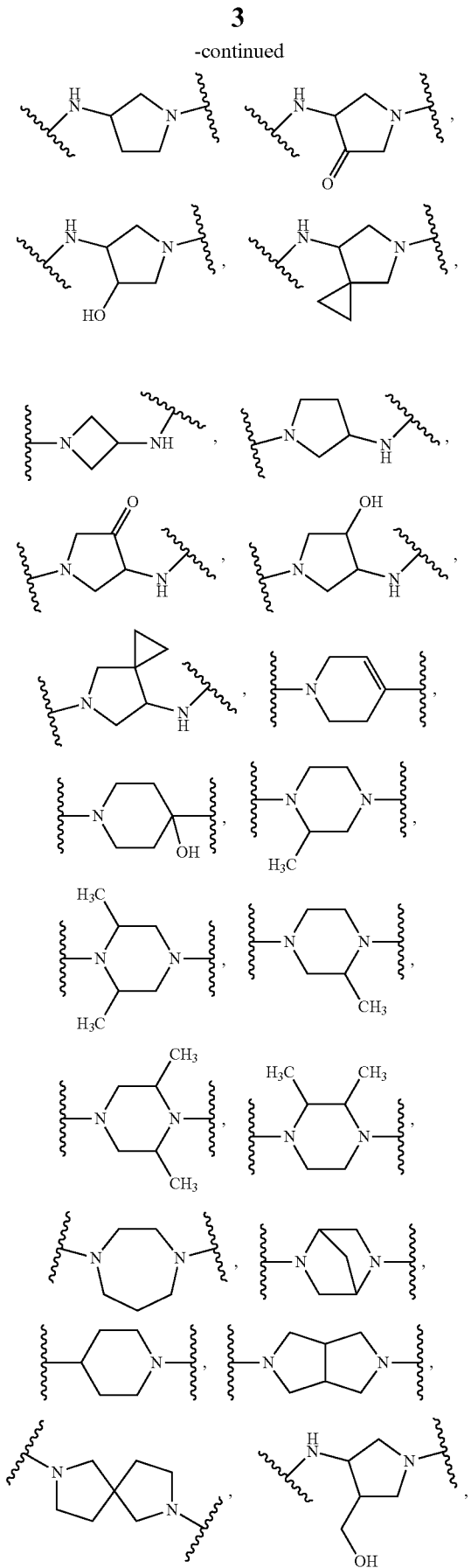

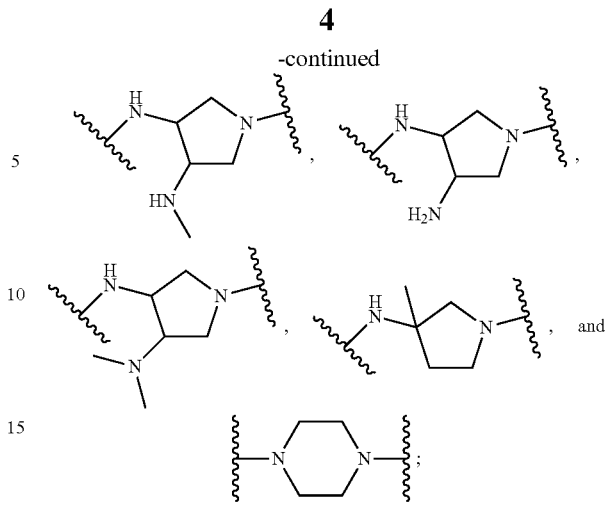

wherein each of $R^{3a}$, $R^{3b}$, and $R^{3c}$ is independently selected from hydrogen, halogen, C1-C4 alkoxy and C1-C4 alkyl, provided at least one of $R^{3a}$, $R^{3b}$, and $R^{3c}$ is halogen; and wherein $R^4$ is selected form hydrogen, halogen, —CN, $SO_2NH_2$, $SO_2CH_3$, $SO_2CF_3$, and $NO_2$, or a pharmaceutically acceptable salt thereof.

Also disclosed are compounds having a structure represented by a formula:

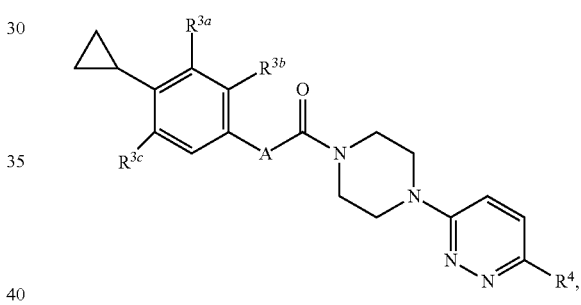

wherein A is selected from O, CO, $CH_2$, $CF_2$, NH, $N(CH_3)$, and CH(OH); wherein each of $R^{3a}$, $R^{3b}$, and $R^{3c}$ is independently selected from hydrogen, halogen, C1-C4 alkoxy and C1-C4 alkyl, provided at least one of $R^{3a}$, $R^{3b}$, and $R^{3c}$ is halogen; and wherein $R^4$ is selected form hydrogen, halogen, —CN, $SO_2NH_2$, $SO_2CH_3$, $SO_2CF_3$, and $NO_2$, or a pharmaceutically acceptable salt thereof.

Also disclosed are methods of making a disclosed compound.

Also disclosed are pharmaceutical compositions comprising at least one disclosed compound.

Also disclosed are methods of modulating pantothenate kinase activity in at least one cell, the method comprising the step of contacting at least one cell with an effective amount of at least one disclosed compound, or a pharmaceutically acceptable salt thereof.

Also disclosed are methods of treating a disorder associated with pantothenate kinase activity in a subject, the method comprising administering to the subject an effective amount of at least one disclosed compound, or a pharmaceutically acceptable salt thereof.

Also disclosed are the method of modulating Coenzyme A levels in cells with an effective amount of at least one disclosed compound, or a pharmaceutically acceptable salt thereof or in combination with Pantothenate and its derivatives.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

A. DEFINITIONS

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

As used in the specification and in the claims, the term "comprising" can include the aspects "consisting of" and "consisting essentially of."

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "about" and "at or about" mean that the amount or value in question can be the value designated some other value approximately or about the same. It is generally understood, as used herein, that it is the nominal value indicated ±10% variation unless otherwise indicated or inferred. The term is intended to convey that similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. It is understood that where "about" is used before a quantitative value, the parameter also includes the specific quantitative value itself, unless specifically stated otherwise.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal A patient refers to a subject afflicted with a disease or disorder. The term "patient" includes human and veterinary subjects.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "dosage form" means a pharmacologically active material in a medium, carrier, vehicle, or device suitable for administration to a subject. A dosage form can comprise a disclosed compound, a product of a disclosed method of making, or a salt, solvate, or polymorph thereof, in combination with a pharmaceutically acceptable excipient, such as a preservative, buffer, saline, or phosphate buffered saline. Dosage forms can be made using conventional pharmaceutical manufacturing and compounding techniques. Dosage forms can comprise inorganic or organic buffers (e.g., sodium or potassium salts of phosphate, carbonate, acetate, or citrate) and pH adjustment agents (e.g., hydrochloric acid, sodium or potassium hydroxide, salts of citrate or acetate, amino acids and their salts) antioxidants (e.g., ascorbic acid, alpha-tocopherol), surfactants (e.g., polysorbate 20, polysorbate 80, polyoxyethylene9-10 nonyl phenol, sodium desoxycholate), solution and/or cryo/lyo stabilizers (e.g., sucrose, lactose, mannitol, trehalose), osmotic adjustment agents (e.g., salts or sugars), antibacterial agents (e.g., benzoic acid, phenol, gentamicin), antifoaming agents (e.g., polydimethylsilozone), preservatives (e.g., thimerosal, 2-phenoxyethanol, EDTA), polymeric stabilizers and viscosity-adjustment agents (e.g., polyvinylpyrrolidone, poloxamer 488, carboxymethylcellulose) and co-solvents (e.g., glycerol, polyethylene glycol, ethanol). A dosage form formulated for injectable use can have a disclosed compound, a product of a disclosed method of making, or a salt, solvate, or polymorph thereof, suspended in sterile saline solution for injection together with a preservative.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used herein, the terms "therapeutic agent" include any synthetic or naturally occurring biologically active compound or composition of matter which, when administered to an organism (human or nonhuman animal), induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index (14$^{th}$ edition), the Physicians' Desk Reference (64$^{th}$ edition), and The Pharmacological Basis of Therapeutics (12$^{th}$ edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrhythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term "therapeutic agent" also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" or "aliphatic group," as used herein, denotes a hydrocarbon moiety that may be straight-chain (i.e., unbranched), branched, or cyclic (including fused, bridging, and spirofused polycyclic) and may be completely saturated or may contain one or more units of unsaturation, but which is not aromatic. Unless otherwise specified, aliphatic groups contain 1-20 carbon atoms. Aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetacosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms. The term alkyl group can also be a C1 alkyl, C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, and the like up to and including a C1-C24 alkyl.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. Alternatively, the term "monohaloalkyl" specifically refers to an alkyl group that is substituted with a single halide, e.g. fluorine, chlorine, bromine, or iodine. The term "polyhaloalkyl" specifically refers to an alkyl group that is independently substituted with two or more halides, i.e. each halide substituent need not be the same halide as another halide substituent, nor do the multiple instances of a halide substituent need to be on the same carbon. The term "alkoxyalkyl" specifically refers to an alkyl group that is substituted with one or more alkoxy groups, as described below. The term "aminoalkyl" specifically refers to an alkyl group that is substituted with one or more amino groups. The term "hydroxyalkyl" specifically refers to an alkyl group that is substituted with one or more hydroxy groups. When "alkyl" is used in one instance and a specific term such as "hydroxyalkyl" is used in another, it is not meant to imply that the term "alkyl" does not also refer to specific terms such as "hydroxyalkyl" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. For example, the cycloalkyl group and heterocycloalkyl group can be substituted with 0, 1, 2, 3, or 4 groups independently selected from C1-C4 alkyl, C3-C7 cycloalkyl, C1-C4 alkoxy, —NH$_2$, (C1-C4) alkylamino, (C1-C4)(C1-C4) dialkylamino, ether, halogen, —OH, C1-C4 hydroxyalkyl, —NO$_2$, silyl, sulfo-oxo, —SH, and C1-C4 thioalkyl, as described herein.

The term "polyalkylene group" as used herein is a group having two or more CH$_2$ groups linked to one another. The polyalkylene group can be represented by the formula —(CH$_2$)$_a$—, where "a" is an integer of from 2 to 500.

The terms "alkoxy" and "alkoxyl" as used herein to refer to an alkyl or cycloalkyl group bonded through an ether linkage; that is, an "alkoxy" group can be defined as —OA$^1$ where $A^1$ is alkyl or cycloalkyl as defined above. "Alkoxy" also includes polymers of alkoxy groups as just described; that is, an alkoxy can be a polyether such as —$OA^1$-$OA^2$ or —$OA^1$-$(OA^2)_a OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. For example, the cycloalkenyl group and heterocycloalkenyl group can be substituted with 0, 1, 2, 3, or 4 groups independently selected from C1-C4 alkyl, C3-C7 cycloalkyl, C1-C4 alkoxy, C2-C4 alkenyl, C3-C6 cycloalkenyl, C2-C4 alkynyl, aryl, heteroaryl, aldeyhyde, —$NH_2$, (C1-C4) alkylamino, (C1-C4)(C1-C4) dialkylamino, carboxylic acid, ester, ether, halogen, —OH, C1-C4 hydroxyalkyl, ketone, azide, —$NO_2$, silyl, sulfo-oxo, —SH, and C1-C4 thioalkyl, as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aromatic group" as used herein refers to a ring structure having cyclic clouds of delocalized π electrons above and below the plane of the molecule, where the π clouds contain (4n+2) π electrons. A further discussion of aromaticity is found in Morrison and Boyd, Organic Chemistry, (5th Ed., 1987), Chapter 13, entitled "Aromaticity," pages 477-497, incorporated herein by reference. The term "aromatic group" is inclusive of both aryl and heteroaryl groups.

The term "aryl" as used herein is a group that contains any carbon-based aromatic group including, but not limited to, benzene, naphthalene, phenyl, biphenyl, anthracene, and the like. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, —$NH_2$, carboxylic acid, ester, ether, halide, hydroxy, ketone, azide, nitro, silyl, sulfo-oxo, or thiol as described herein. The term "biaryl" is a specific type of aryl group and is included in the definition of "aryl." In addition, the aryl group can be a single ring structure or comprise multiple ring structures that are either fused ring structures or attached via one or more bridging groups such as a carbon-carbon bond. For example, biaryl can be two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" or "CO" is a short hand notation for a carbonyl group, i.e., C=O.

The terms "amine" or "amino" as used herein are represented by the formula —$NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein. A specific example of amino is —$NH_2$.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —$OC(O)A^1$ or —$C(O)OA^1$, where $A^1$ can be alkyl, cycloalkyl, alkenyl, cycloalkenyl, alkynyl, cycloalkynyl, aryl, or heteroaryl group as described herein. The term "polyester" as used herein is represented by the formula -$(A^1O(O)C-A^2-C(O)O)_a$— or -$(A^1O(O)C-A^2-OC(O))_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1OA^2$, where $A^1$ and $A^2$ can be, independently, an alkyl, cycloalkyl, alkenyl, cycloalkenyl, alkynyl, cycloalkynyl, aryl, or heteroaryl group described herein. The term "polyether" as used herein is represented by the formula where $A^1$ and $A^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The terms "halo," "halogen," or "halide," as used herein can be used interchangeably and refer to F, Cl, Br, or I.

The terms "pseudohalide," "pseudohalogen," or "pseudohalo," as used herein can be used interchangeably and refer to functional groups that behave substantially similar to halides. Such functional groups include, by way of example, cyano, thiocyanato, azido, trifluoromethyl, trifluoromethoxy, perfluoroalkyl, and perfluoroalkoxy groups.

The term "heteroalkyl," as used herein refers to an alkyl group containing at least one heteroatom. Suitable heteroatoms include, but are not limited to, 0, N, Si, P and S, wherein the nitrogen, phosphorous and sulfur atoms are optionally oxidized, and the nitrogen heteroatom is optionally quaternized. Heteroalkyls can be substituted as defined above for alkyl groups.

The term "heteroaryl," as used herein refers to an aromatic group that has at least one heteroatom incorporated within the ring of the aromatic group. Examples of heteroatoms include, but are not limited to, nitrogen, oxygen, sulfur, and phosphorus, where N-oxides, sulfur oxides, and dioxides are permissible heteroatom substitutions. The heteroaryl group can be substituted or unsubstituted. The heteroaryl group can be substituted with one or more groups including, but not limited to, alkyl, cycloalkyl, alkoxy, amino, ether, halide, hydroxy, nitro, silyl, sulfo-oxo, or thiol as described herein. Heteroaryl groups can be monocyclic, or alternatively fused ring systems. Heteroaryl groups include, but are not limited to, furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, and pyrazolopyrimidinyl. Further not limiting examples of heteroaryl groups include, but are not limited to, pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl.

The terms "heterocycle" or "heterocyclyl," as used herein can be used interchangeably and refer to single and multi-cyclic aromatic or non-aromatic ring systems in which at least one of the ring members is other than carbon. Thus, the term is inclusive of, but not limited to, "heterocycloalkyl", "heteroaryl", "bicyclic heterocycle" and "polycyclic heterocycle." Heterocycle includes pyridine, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridazine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like. The term heterocyclyl group can also be a C2 heterocyclyl, C2-C3 heterocyclyl, C2-C4 heterocyclyl, C2-C5 heterocyclyl, C2-C6 heterocyclyl, C2-C7 heterocyclyl, C2-C8 heterocyclyl, C2-C9 heterocyclyl, C2-C10 heterocyclyl, C2-C11 heterocyclyl, and the like up to and including a C2-C18 heterocyclyl. For example, a C2 heterocyclyl comprises a group which has two carbon atoms and at least one heteroatom, including, but not limited to, aziridinyl, diazetidinyl, dihydrodiazetyl, oxiranyl, thiiranyl, and the like. Alternatively, for example, a C5 heterocyclyl comprises a group which has five carbon atoms and at least one heteroatom, including, but not limited to, piperidinyl, tetrahydropyranyl, tetrahydrothiopyranyl, diazepanyl, pyridinyl, and the like. It is understood that a heterocyclyl group may be bound either through a heteroatom in the ring, where chemically possible, or one of carbons comprising the heterocyclyl ring.

The term "bicyclic heterocycle" or "bicyclic heterocyclyl," as used herein refers to a ring system in which at least one of the ring members is other than carbon. Bicyclic heterocyclyl encompasses ring systems wherein an aromatic ring is fused with another aromatic ring, or wherein an aromatic ring is fused with a non-aromatic ring. Bicyclic heterocyclyl encompasses ring systems wherein a benzene ring is fused to a 5- or a 6-membered ring containing 1, 2 or 3 ring heteroatoms or wherein a pyridine ring is fused to a 5- or a 6-membered ring containing 1, 2 or 3 ring heteroatoms. Bicyclic heterocyclic groups include, but are not limited to, indolyl, indazolyl, pyrazolo[1,5-a]pyridinyl, benzofuranyl, quinolinyl, quinoxalinyl, 1,3-benzodioxolyl, 2,3-dihydro-1,4-benzodioxinyl, 3,4-dihydro-2H-chromenyl, 1H-pyrazolo[4,3-c]pyridin-3-yl; 1H-pyrrolo[3,2-b]pyridin-3-yl; and 1H-pyrazolo[3,2-b]pyridin-3-yl.

The term "heterocycloalkyl" as used herein refers to an aliphatic, partially unsaturated or fully saturated, 3- to 14-membered ring system, including single rings of 3 to 8 atoms and bi- and tricyclic ring systems. The heterocycloalkyl ring-systems include one to four heteroatoms independently selected from oxygen, nitrogen, and sulfur, wherein a nitrogen and sulfur heteroatom optionally can be oxidized and a nitrogen heteroatom optionally can be substituted. Representative heterocycloalkyl groups include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "hydroxy" or "hydroxyl" as used herein is represented by the formula —OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" or "azido" as used herein is represented by the formula —$N_3$.

The term "nitro" as used herein is represented by the formula —$NO_2$.

The term "nitrile" or "cyano" as used herein is represented by the formula —CN or —CN.

The term "silyl" as used herein is represented by the formula —$SiA^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —S(O)A$^1$, —S(O)$_2$A$^1$, —OS(O)$_2$A$^1$, or —OS(O)$_2$OA$^1$, where A$^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —S(O)$_2$A$^1$, where A$^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula A$^1$S(O)$_2$A$^2$, where A$^1$ and A$^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula A$^1$S(O)A$^2$, where A$^1$ and A$^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"R$^1$," "R$^2$," "R$^3$," "R$^n$," where n is an integer, as used herein can, independently, possess one or more of the groups listed above. For example, if R$^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogen of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; —(CH$_2$)$_{0-4}$R°; —(CH$_2$)$_{0-4}$OR°; —O(CH$_2$)$_{0-4}$R°, —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH=CHPh, which may be substituted with R°; —(CH$_2$)$_{0-4}$O(CH$_2$)$_{0-1}$-pyridyl which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR—, SC(S)SR°; —(CH$_2$)$_{0-4}$SC(O)R°; —(CH$_2$)$_{0-4}$C(O)NR°$_2$; —C(S)NR°$_2$; —C(S)SR°; —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched)alkylene)O—N(R°$_2$); or —(C$_{1-4}$ straight or branched)alkylene)C(O)O—N(R°$_2$), wherein each R° may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$ SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet_2$, —NO$_2$, —C(O)SR$^\bullet$, —(C$_{1-4}$ straight or branched alkylene)C(O)OR$^\bullet$, or —SRR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R$^\bullet$ include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_{1-4}$ aliphatic, —CH₂Ph, —O(CH₂)₀₋₁Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R†, —NR†₂, —C(O)R†, —C(O)OR†, —C(O)C(O)R†, —C(O)CH₂C(O)R†, —S(O)₂R†, —S(O)₂NR†₂, —C(S)NR†₂, —C(NH)NR†₂, or —N(R†)S(O)₂R†; wherein each R† is independently hydrogen, C₁₋₆ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R†, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R† are independently halogen, —R•, -(haloR•), —OH, —OR•, —O(haloR•), —CN, —C(O)OH, —C(O)OR•, —NH₂, —NHR•, —NR•₂, or —NO₂, wherein each R• is unsubstituted or where preceded by "halo" is substituted only with one or more halogens, and is independently C₁₋₄ aliphatic, —CH₂Ph, —O(CH₂)₀₋₁Ph, or a 5-6-membered saturated, partially unsaturated, or aryl ring having 0-4 heteroatoms independently selected from nitrogen, oxygen, or sulfur.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, triflate, mesylate, tosylate, and brosylate.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure:

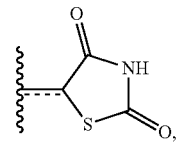

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5, 6, 7, 8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but are not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Ingold-Prelog system can be used to assign the (R) or (S) configuration to a chiral carbon.

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvent or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

It is also appreciated that certain compounds described herein can be present as an equilibrium of tautomers. For example, ketones with an α-hydrogen can exist in an equilibrium of the keto form and the enol form.

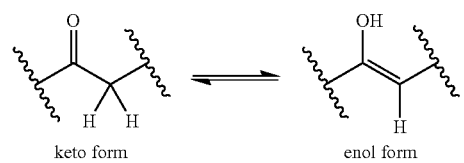

keto form    enol form

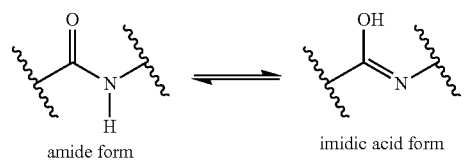

amide form    imidic acid form

Likewise, amides with an N-hydrogen can exist in an equilibrium of the amide form and the imidic acid form. As another example, pyrazoles can exist in two tautomeric forms, $N^1$-unsubstituted, 3-$A^3$ and $N^1$-unsubstituted, 5-$A^3$ as shown below.

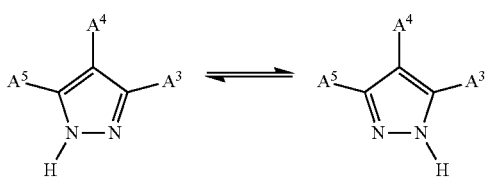

Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

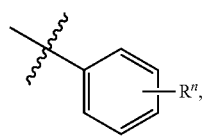

which is understood to be equivalent to a formula:

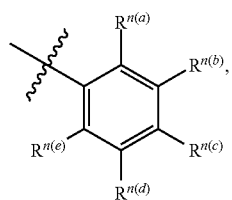

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and supplemental volumes (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. COMPOUNDS

In one aspect, disclosed are compounds useful in treating or preventing a disorder associated with PanK activity such as, for example, PKAN and diabetes. In a further aspect, the disclosed compounds exhibit modulation of PanK activity. In a still further aspect, the disclosed compounds exhibit inhibition of PanK activity. In yet a further aspect, the disclosed compounds exhibit activation of PanK activity.

In one aspect, the compounds of the invention are useful in the treatment or prevention of disorders associated with PanK dysfunction and other diseases in which PanKs or altered levels of CoA and CoA esters are involved, as further described herein.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Structure

In one aspect, disclosed are compounds having a structure represented by a formula:

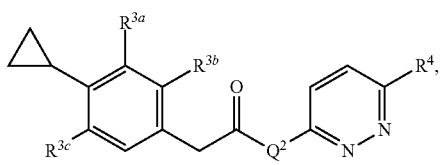

wherein $Q^2$ is a structure selected from:

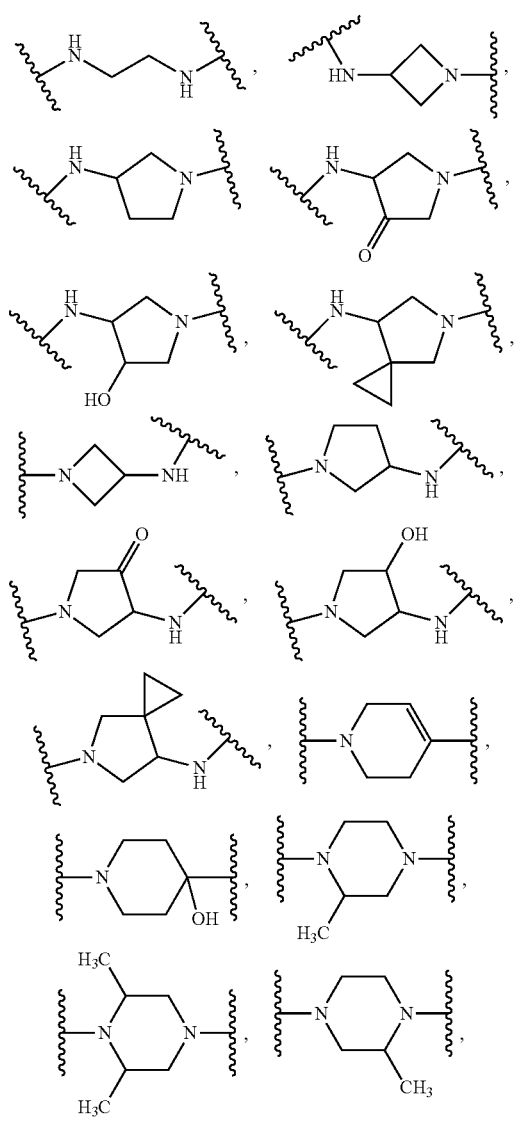

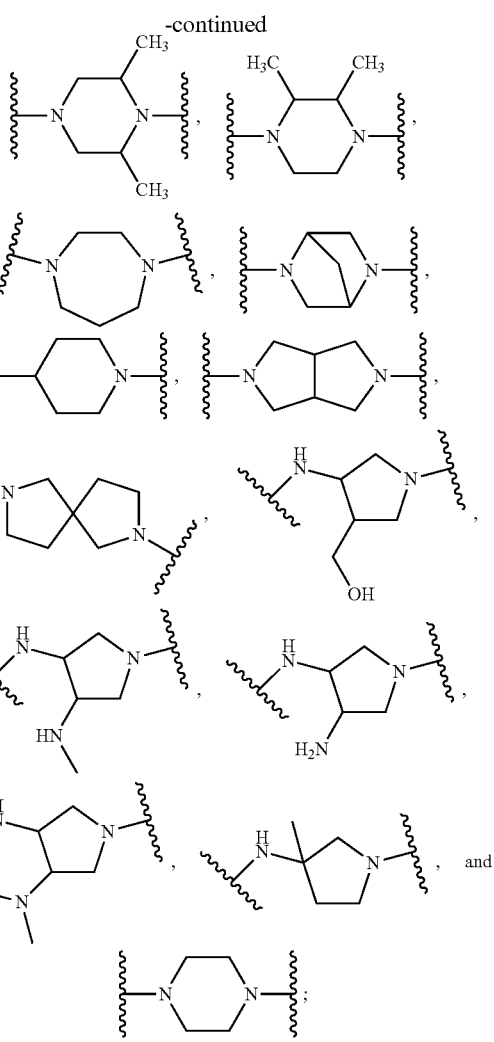

wherein each of $R^{3a}$, $R^{3b}$, and $R^{3c}$ is independently selected from hydrogen, halogen, C1-C4 alkoxy and C1-C4 alkyl, provided at least one of $R^{3a}$, $R^{3b}$, and $R^{3c}$ is halogen; and wherein $R^4$ is selected form hydrogen, halogen, —CN, $SO_2NH_2$, $SO_2CH_3$, $SO_2CF_3$, and $NO_2$, or a pharmaceutically acceptable salt thereof.

In one aspect, disclosed are compounds having a structure represented by a formula:

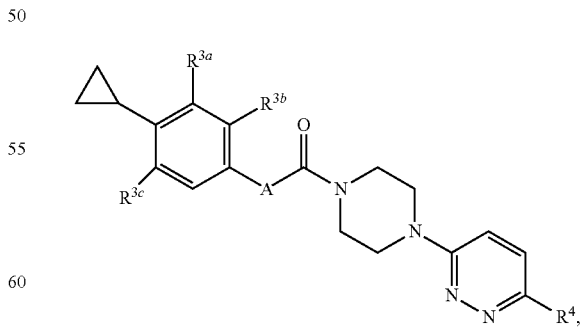

wherein A is selected from O, CO, $CH_2$, $CF_2$, NH, $N(CH_3)$, and CH(OH); wherein each of $R^{3a}$, $R^{3b}$, and $R^{3c}$ is independently selected from hydrogen, halogen, C1-C4 alkoxy and C1-C4 alkyl, provided at least one of $R^{3a}$, $R^{3b}$, and $R^{3c}$ is halogen; and wherein R⁴ is selected form hydrogen, halogen, —CN, SO₂NH₂, SO₂CH₃, SO₂CF₃, and NO₂, or a pharmaceutically acceptable salt thereof.

In a further aspect, the compound has a structure represented by a formula:

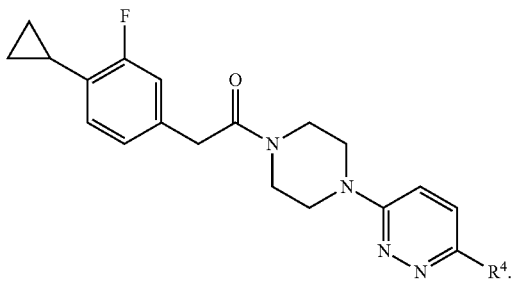

In a further aspect, the compound is selected from:

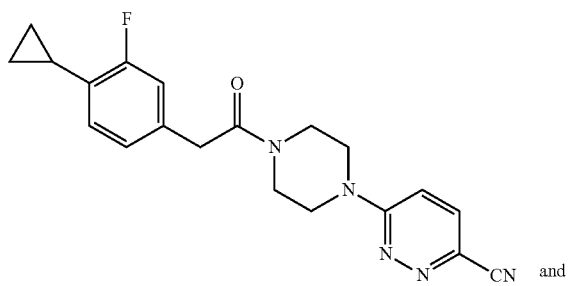
and

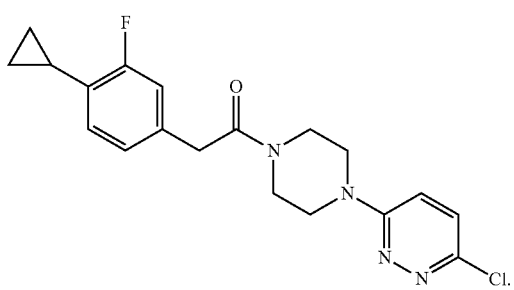

In a further aspect, the compound is selected from:

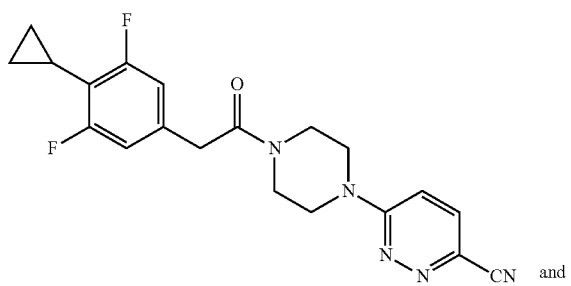
and

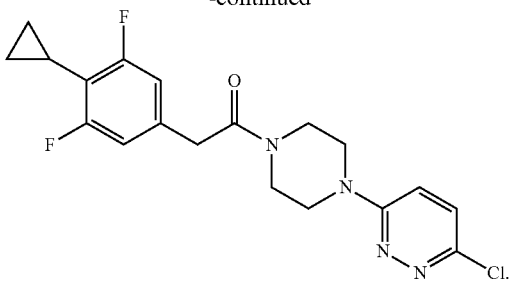

In a further aspect, the compound is selected from:

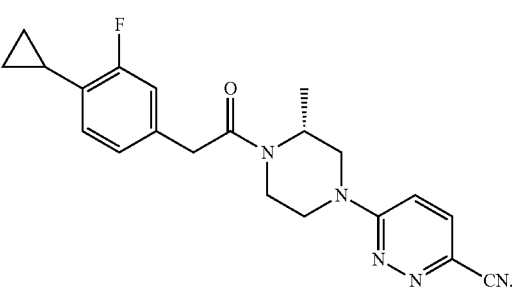

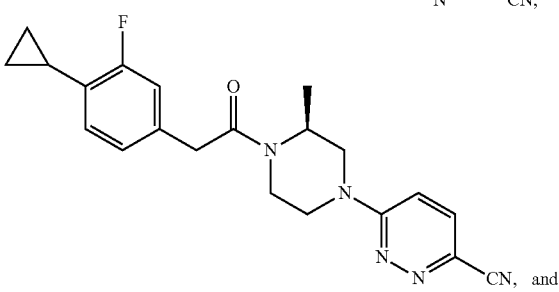
and a. A Groups

In one aspect, A is selected from O, CO, CH₂, CF₂, NH, N(CH₃), and CH(OH). In one aspect, A is selected from O, CO, CH₂, CF₂, NH, and CH(OH). In one aspect, O, CO, CH₂, CF₂, N(CH₃), and CH(OH). In one aspect, A is selected from O, CO, CH₂, CF₂, and CH(OH).

In a further aspect, A is selected from O, CO, CH₂, and CF₂. In a still further aspect, A is selected from O, CO, and CH₂. In yet a further aspect, A is selected from O and CO. In an even further aspect, A is O. In a still further aspect, A is CO. In yet a further aspect, A is CH₂. In an even further aspect, A is CF₂.

In a further aspect, A is selected from NH and N(CH₃). In a still further aspect, A is NH. In yet a further aspect, A is N(CH₃).

In a further aspect, A is selected from NH and CH₂.

In a further aspect, A is CH(OH).

b. $Q^2$ Groups
In one aspect, $Q^2$ is a structure selected from:
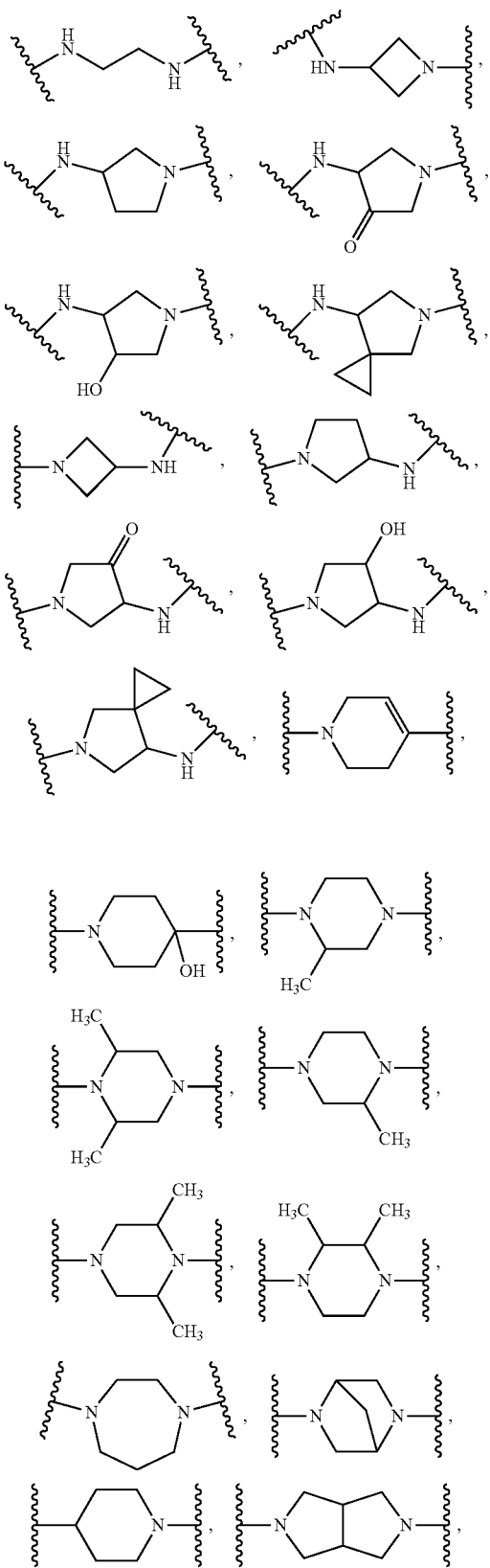
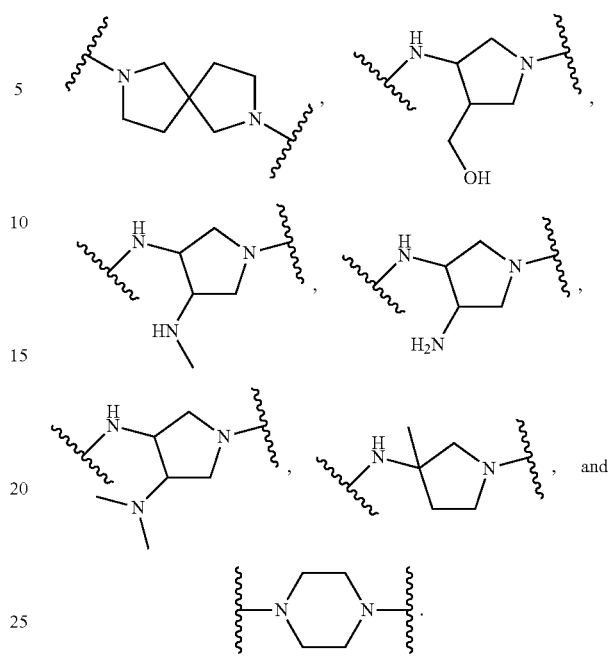
In one aspect, $Q^2$ is a structure selected from:
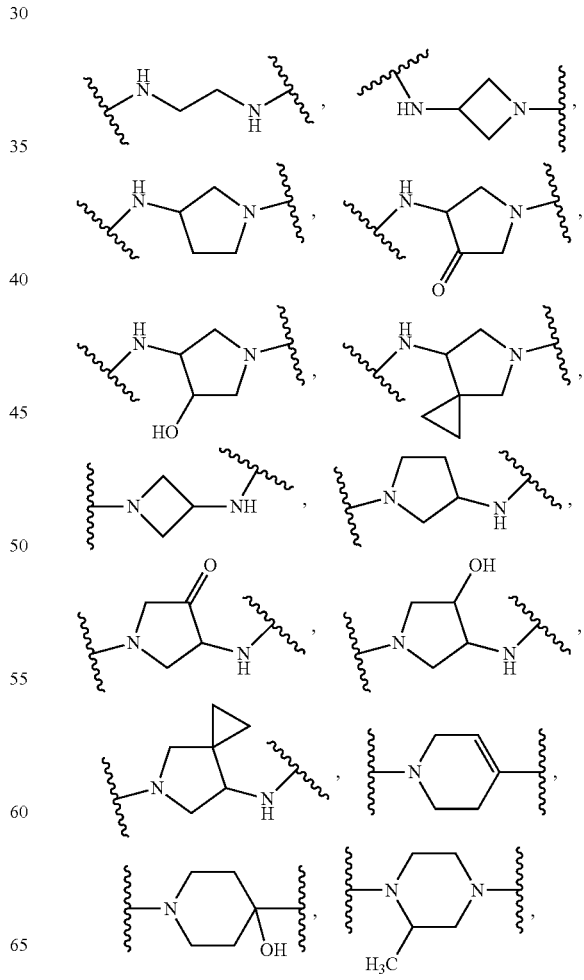

-continued
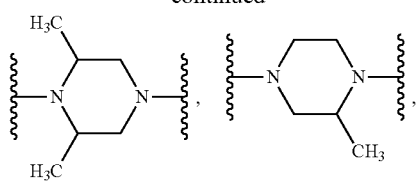
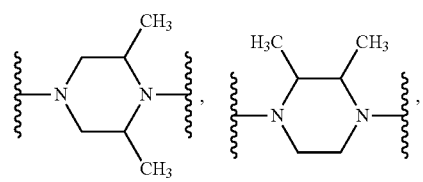
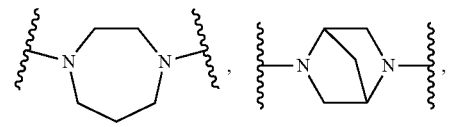
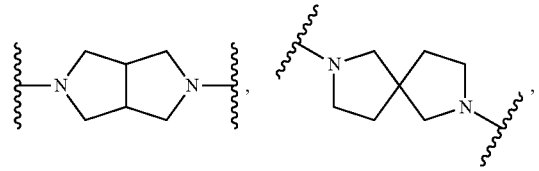
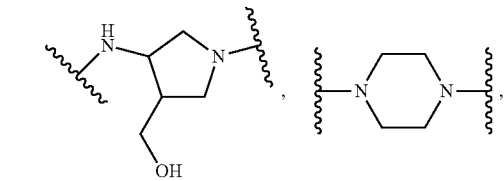
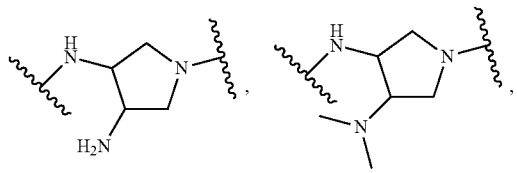
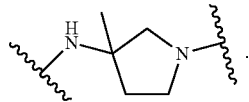
In a further aspect, $Q^2$ is a structure selected from:
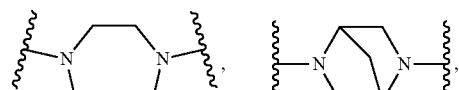
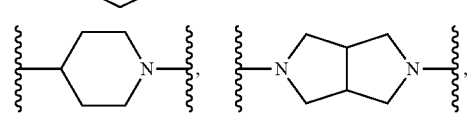
-continued
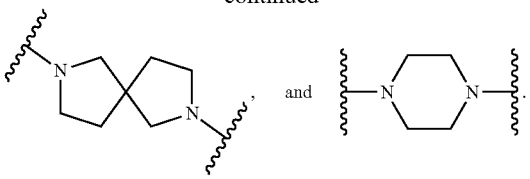, and 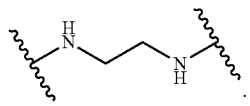 [SMILES: *NCCN*].
In a still further aspect, $Q^2$ is:
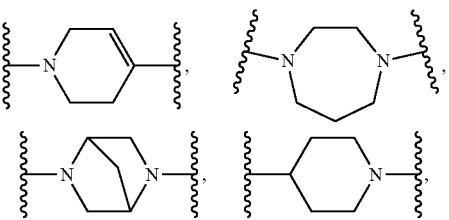
In yet a further aspect, $Q^2$ is a structure selected from:
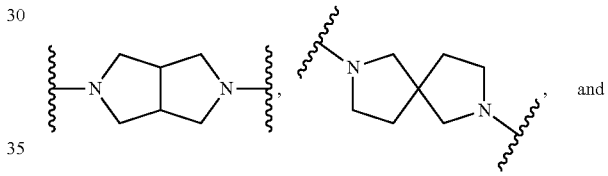
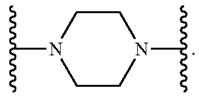.
In an even further aspect, $Q^2$ is a structure selected from:
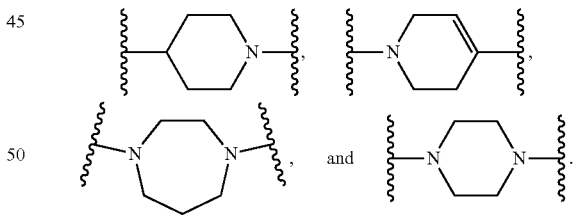
In a still further aspect, $Q^2$ is a structure selected from:
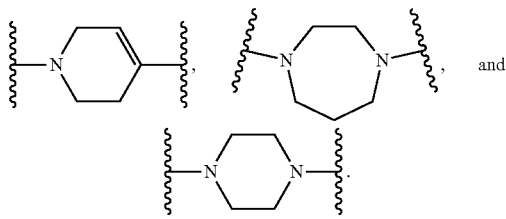

In yet a further aspect, $Q^2$ is a structure selected from:
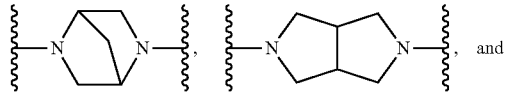
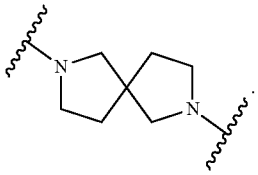
In a further aspect, $Q^2$ is a structure selected from:
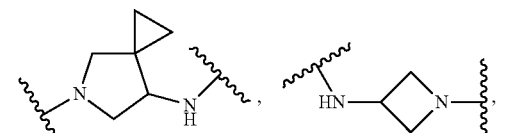
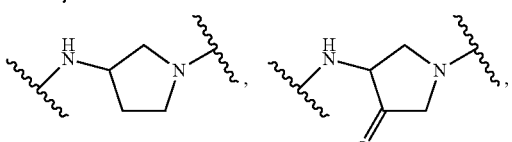
-continued
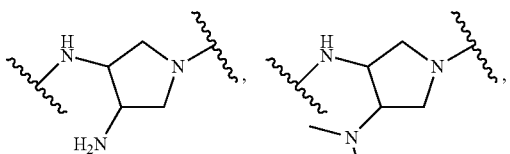
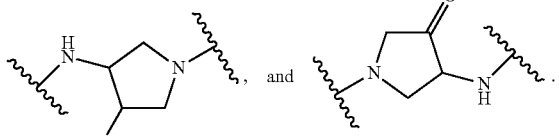
In a still further aspect, $Q^2$ is a structure selected from:
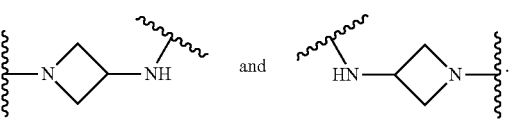 [SMILES: *NC1CN(*)C1 ; *NC1CN(*)C1]
In yet a further aspect, $Q^2$ is a structure selected from:
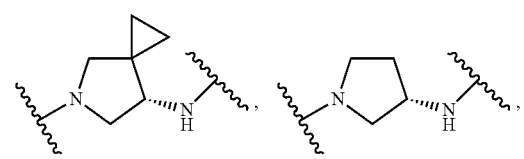
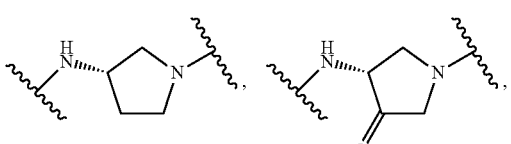
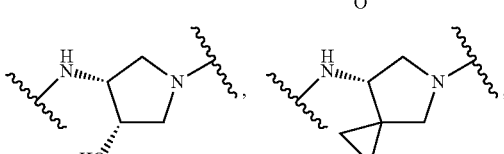
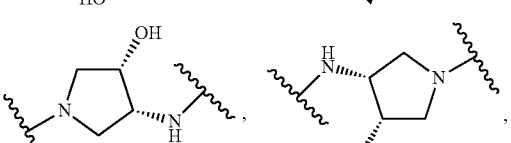
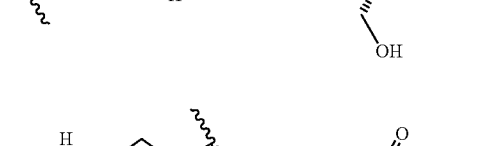
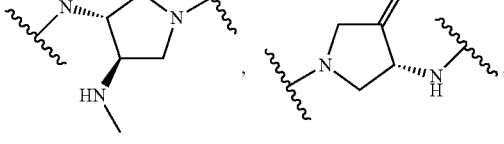

-continued
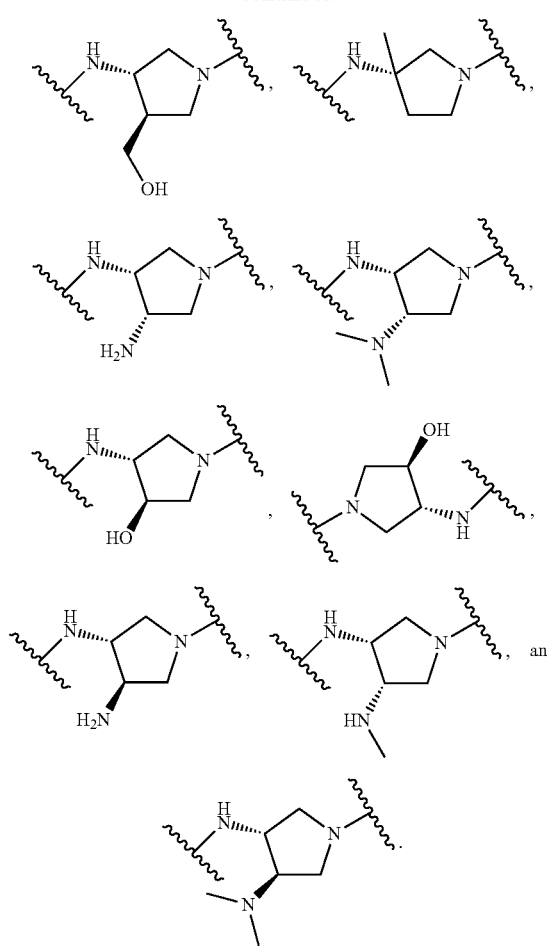
In an even further aspect, $Q^2$ is a structure selected from:
In a still further aspect, $Q^2$ is a structure selected from:
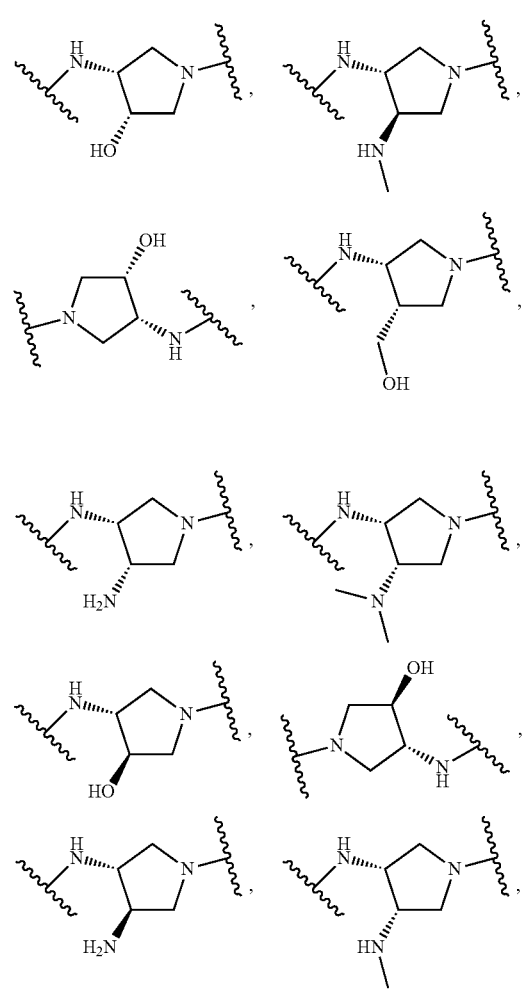
In yet a further aspect, $Q^2$ is a structure selected from:
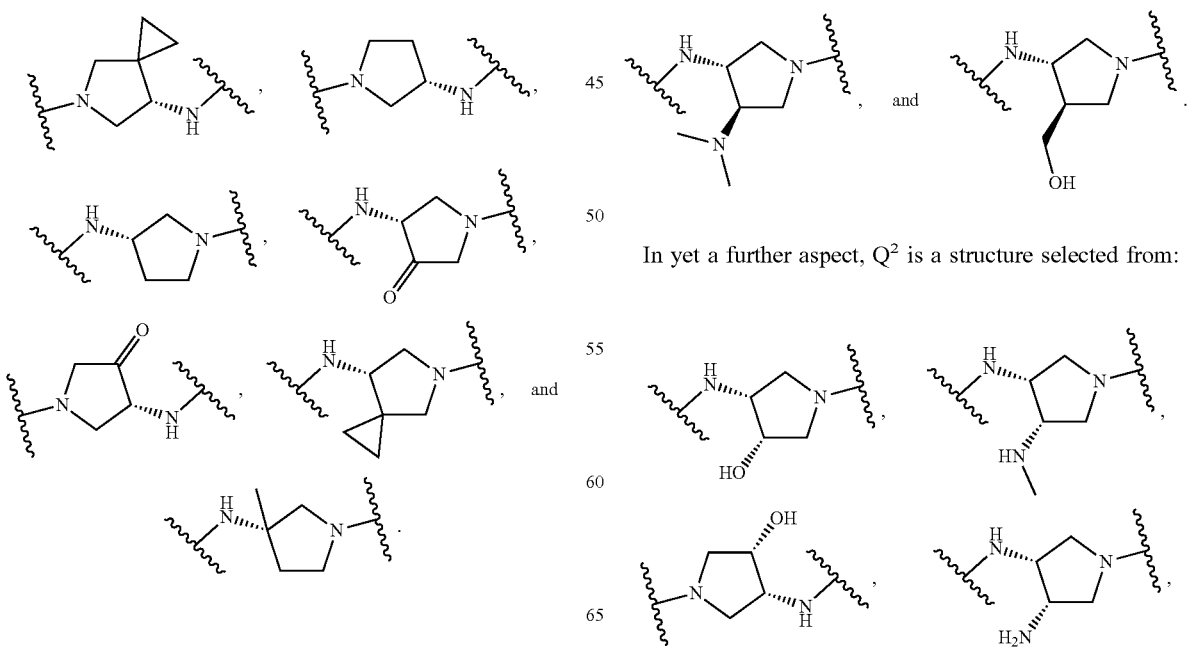

-continued
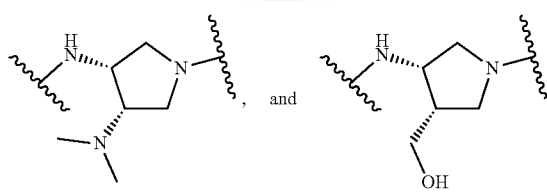
In an even further aspect, $Q^2$ is a structure selected from:
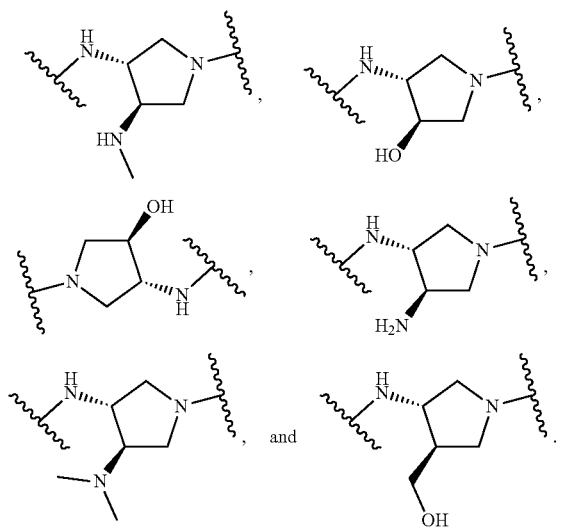
In a still further aspect, $Q^2$ is a structure selected from:
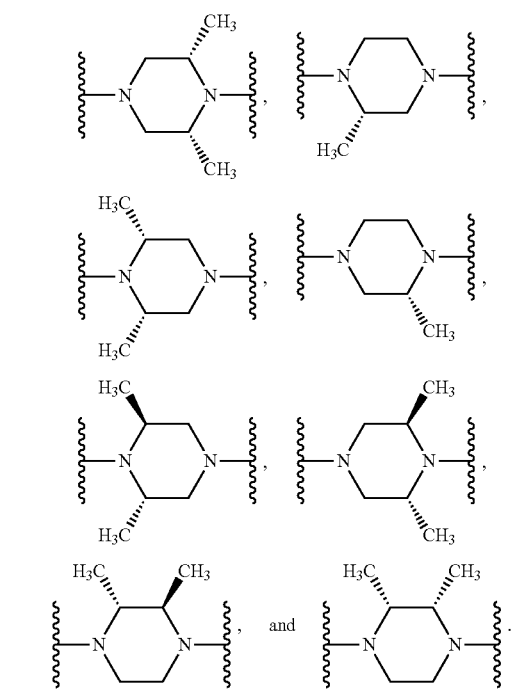
In yet a further aspect, $Q^2$ is a structure selected from:
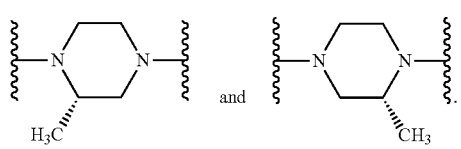
In an even further aspect, $Q^2$ is a structure selected from:
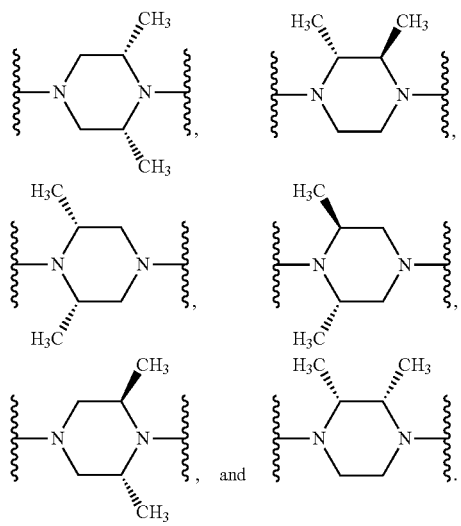
In a still further aspect, $Q^2$ is a structure selected from:
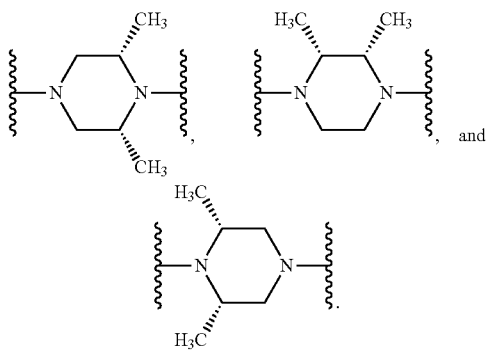
In yet a further aspect, $Q^2$ is a structure selected from:
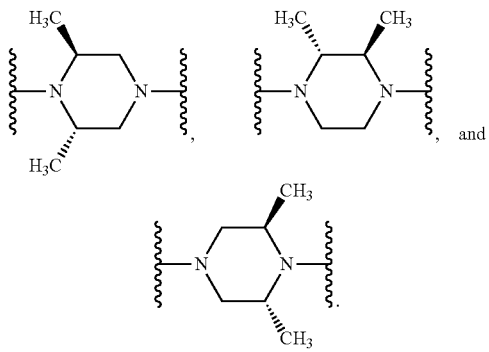

In a further aspect, $Q^2$ is a structure selected from:
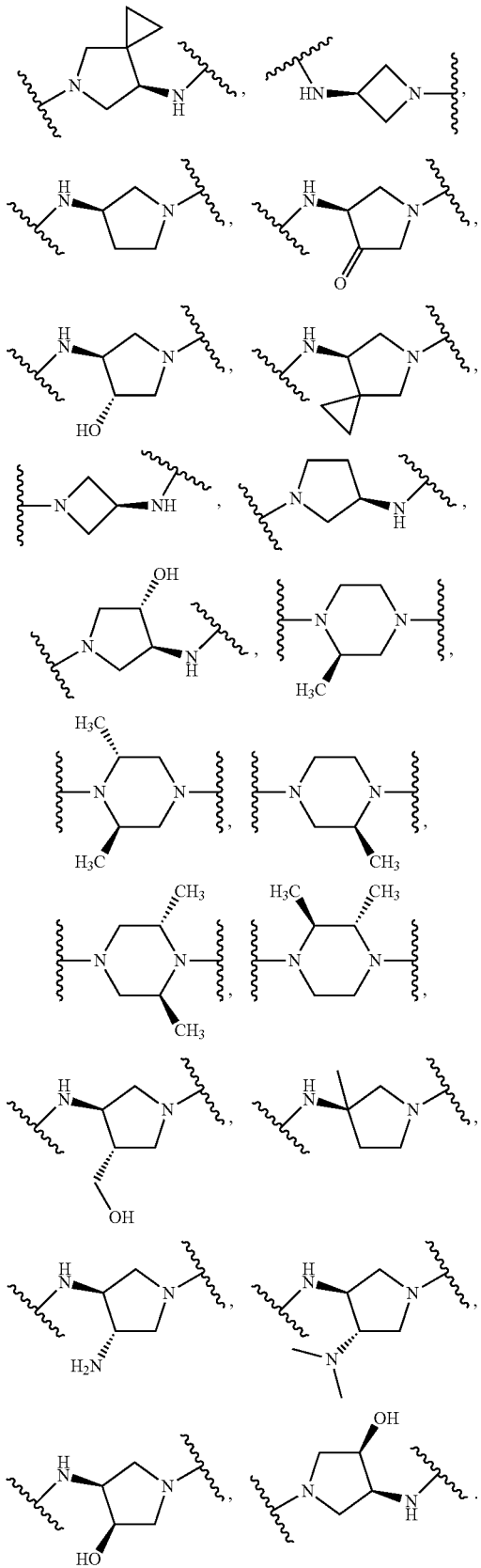
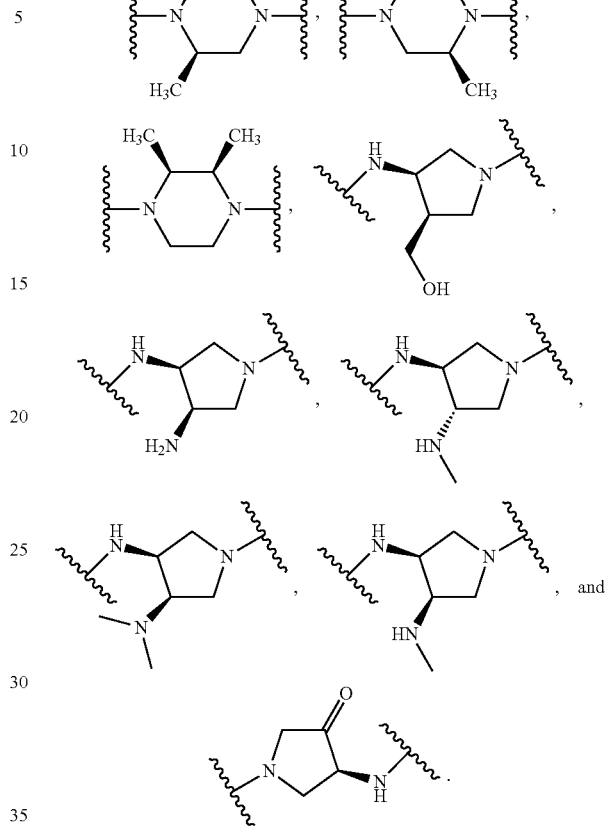
In a still further aspect, $Q^2$ is a structure selected from:
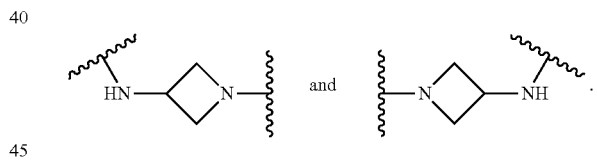
In yet a further aspect, $Q^2$ is a structure selected from:
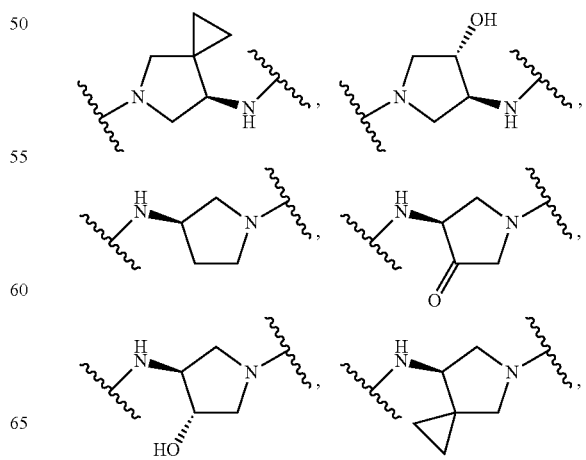

-continued
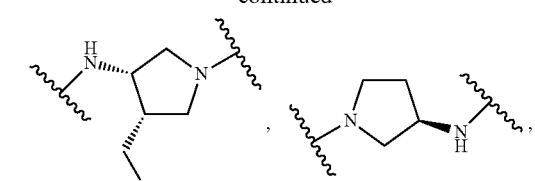
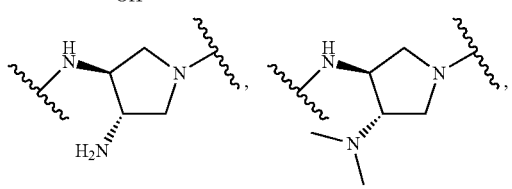
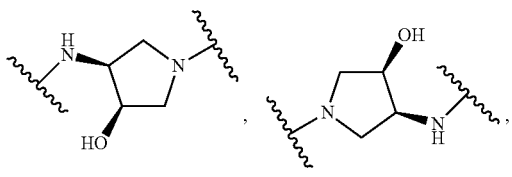
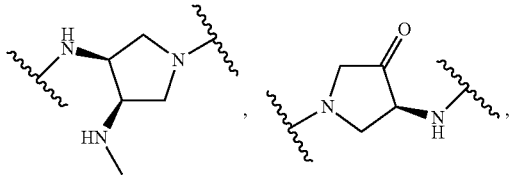
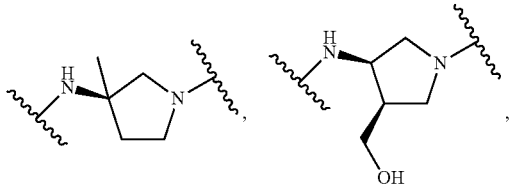
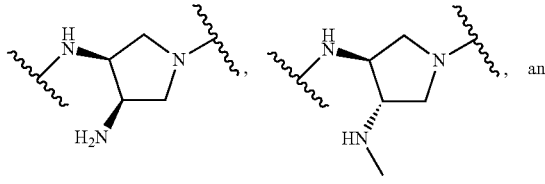
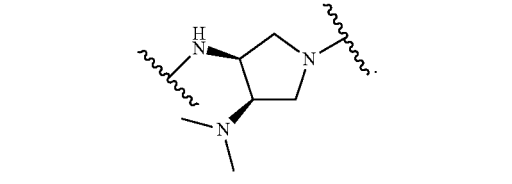
In an even further aspect, $Q^2$ is a structure selected from:
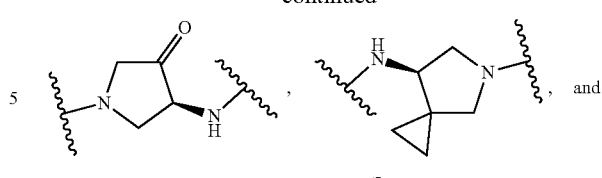, and
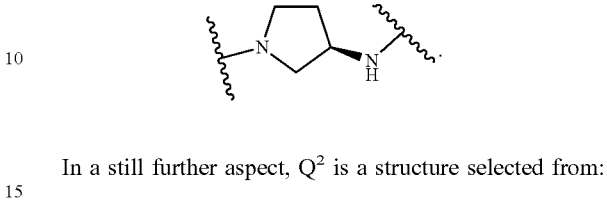
In a still further aspect, $Q^2$ is a structure selected from:
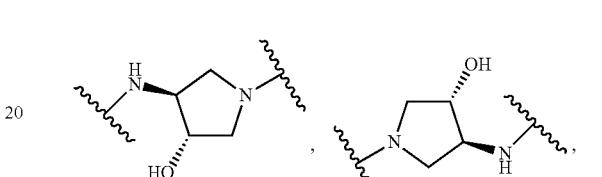
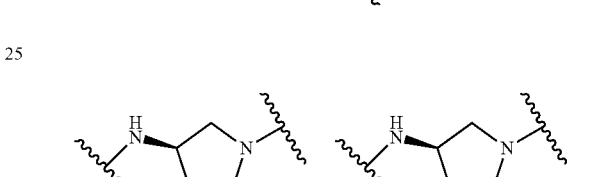
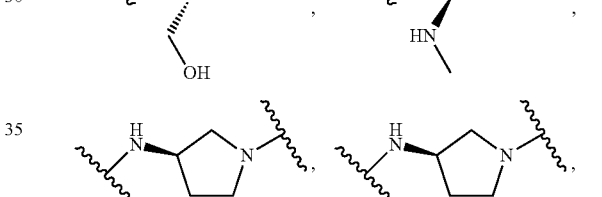
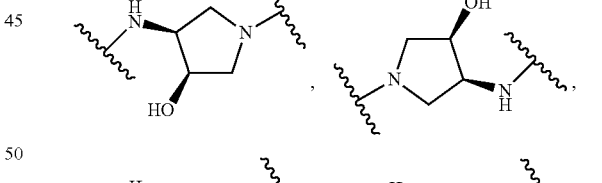
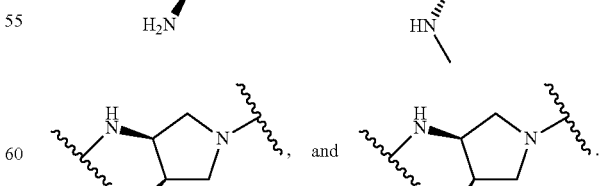, and

In yet a further aspect, $Q^2$ is a structure selected from:
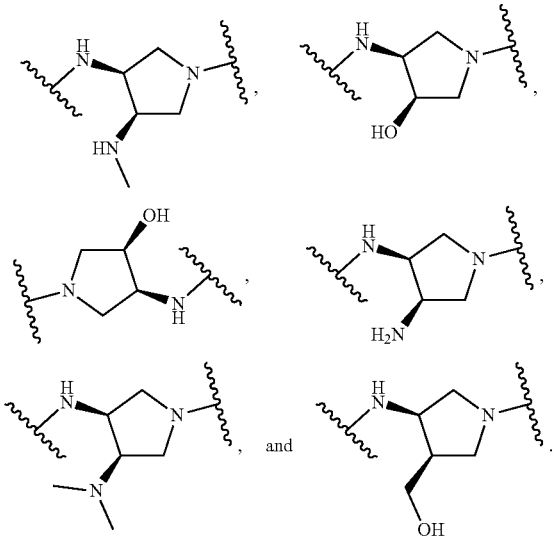
In an even further aspect, $Q^2$ is a structure selected from:
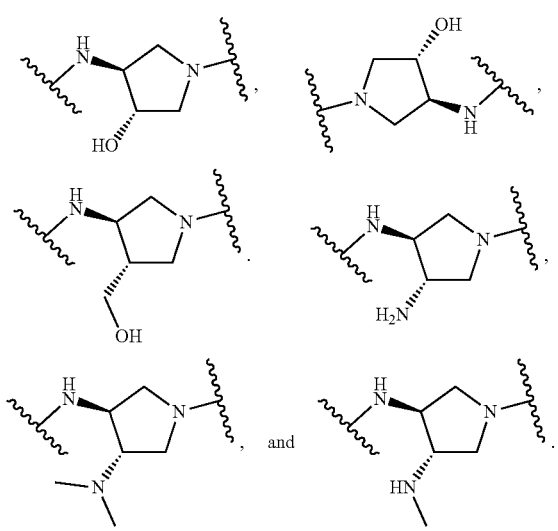
In a still further aspect, $Q^2$ is a structure selected from:
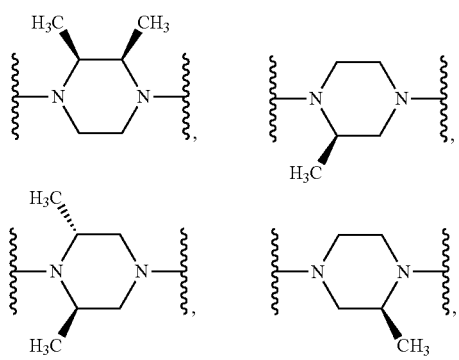
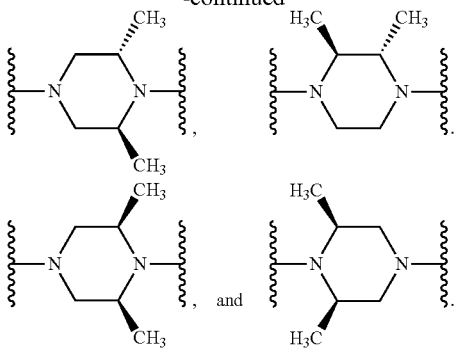
In yet a further aspect, $Q^2$ is a structure selected from:
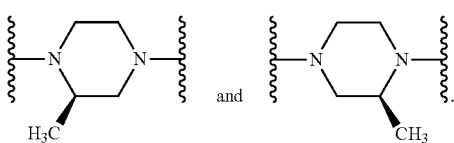
In an even further aspect, $Q^2$ is a structure selected from:
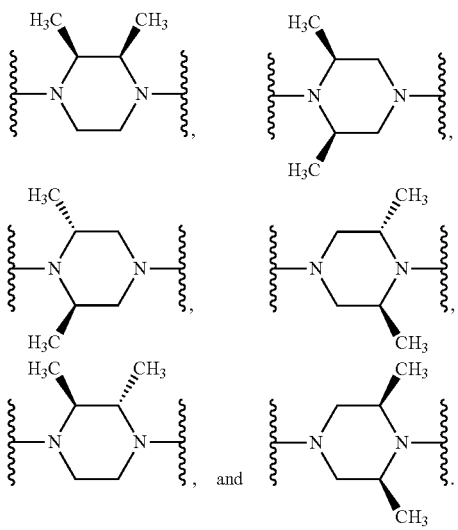
In a still further aspect, $Q^2$ is a structure selected from:
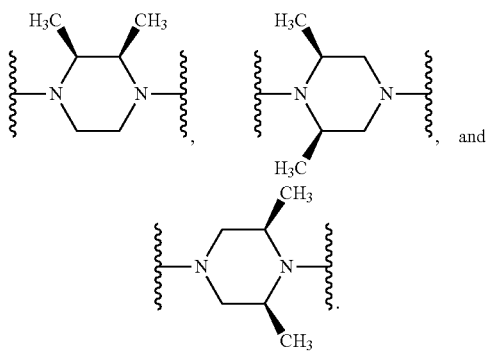

In yet a further aspect, $Q^2$ is a structure selected from:

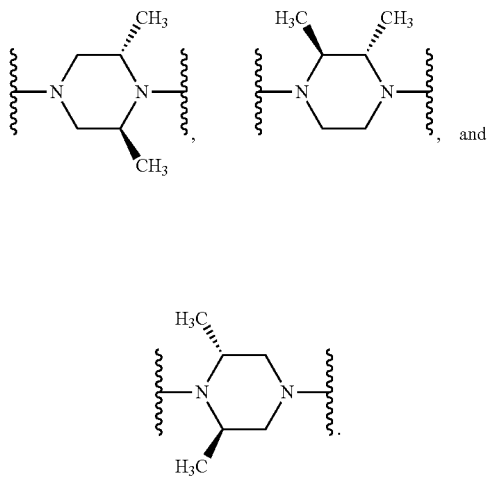

In a further aspect, $Q^2$ is a structure:

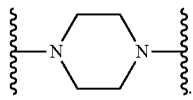 [SMILES: *N1CCN(*)CC1]

C. $R^{3A}$, $R^{3B}$, and $R^{3C}$ Groups

In one aspect, each of $R^{3a}$, $R^{3b}$, and $R^{3c}$ is independently selected from hydrogen, halogen, C1-C4 alkoxy and C1-C4 alkyl, provided at least one of $R^{3a}$, $R^{3b}$, and $R^{3c}$ is halogen. In a further aspect, each of $R^{3b}$ and $R^{3c}$ is hydrogen. In a still further aspect, each of $R^{3a}$ and $R^{3c}$ is hydrogen. In yet a further aspect, each of $R^{3a}$ and $R^{3b}$ is hydrogen.

In a further aspect, each of $R^{3a}$, $R^{3b}$, and $R^{3c}$ is independently selected from hydrogen, —F, —Br, methyl, ethyl, n-propyl, i-propyl, n-butyl, i-butyl, t-butyl, and s-butyl. In a still further aspect, each of $R^{3a}$, $R^{3b}$, and $R^{3c}$ is independently selected from hydrogen, —F, —Br, methyl, ethyl, n-propyl, and i-propyl. In yet a further aspect, each of $R^{3a}$, $R^{3b}$, and $R^{3c}$ is is independently selected from hydrogen, —F, —Cl, —Br, methyl, and ethyl. In an even further aspect, each of $R^{3a}$, $R^{3b}$, and $R^{3c}$ is independently selected from hydrogen, —F, —Br, and methyl.

In a further aspect, each of $R^{3a}$, $R^{3b}$, and $R^{3c}$ is independently selected from hydrogen, —F, —Br, methyl, ethyl, n-propyl, i-propyl, —OCH$_3$, —OCH$_2$CH$_3$, —O(CH$_2$)$_2$CH$_3$, and —OCH(CH$_3$)$_2$. In a still further aspect, each of $R^{3a}$, $R^{3b}$, and $R^{3c}$ is independently selected from hydrogen, —F, —Cl, —Br, methyl, ethyl, —OCH$_3$, and —OCH$_2$CH$_3$. In yet a further aspect, each of $R^{3a}$, $R^{3b}$, and $R^{3c}$ is independently selected from hydrogen, —F, —Br, methyl, and —OCH$_3$.

In a further aspect, each of $R^{3a}$, $R^{3b}$, and $R^{3c}$ is independently selected from hydrogen and C1-C4 alkyl. In a still further aspect, each of $R^{3a}$, $R^{3b}$, and $R^{3c}$ is independently selected from hydrogen, methyl, ethyl, n-propyl, and i-propyl. In yet a further aspect, each of $R^{3a}$, $R^{3b}$, and $R^{3c}$ is independently selected from hydrogen, methyl, and ethyl. In an even further aspect, each of $R^{3a}$, $R^{3b}$, and $R^{3c}$ is independently selected from hydrogen and ethyl. In a still further aspect, each of $R^{3a}$, $R^{3b}$, and $R^{3c}$ is independently selected from hydrogen and methyl.

In a further aspect, each of $R^{3a}$, $R^{3b}$, and $R^{3c}$ is independently selected from hydrogen, —F, and —Br. In a still further aspect, each of $R^{3a}$, $R^{3b}$, and $R^{3c}$ is independently selected from hydrogen, —F, and —Cl. In yet a further aspect, each of $R^{3a}$, $R^{3b}$, and $R^{3c}$ is independently selected from hydrogen and —I. In an even further aspect, each of $R^{3a}$, $R^{3b}$, and $R^{3c}$ is independently selected from hydrogen and —Br. In a still further aspect, each of $R^{3a}$, $R^{3b}$, and $R^{3c}$ is independently selected from hydrogen and —Cl. In yet a further aspect, each of $R^{3a}$, $R^{3b}$, and $R^{3c}$ is independently selected from hydrogen and —F.

In a further aspect, $R^{3a}$ is halogen. In a still further aspect, $R^{3a}$ is selected from —F, —Cl, and —Br. In yet a further aspect, $R^{3a}$ is —F.

In a further aspect, $R^{3a}$ is halogen and each of $R^{3b}$ and $R^{3c}$ is hydrogen. In a still further aspect, $R^{3a}$ is selected from —F, —Cl, and —Br, and each of $R^{3b}$ and $R^{3c}$ is hydrogen. In yet a further aspect, $R^{3a}$ is —F and each of $R^{3b}$ and $R^{3c}$ is hydrogen.

In a further aspect, $R^{3b}$ is halogen. In a still further aspect, $R^{3b}$ is selected from —F, —Cl, and —Br. In yet a further aspect, $R^{3b}$ is —F.

In a further aspect, $R^{3b}$ is halogen and each of $R^{3a}$ and $R^{3c}$ is hydrogen. In a still further aspect, $R^{3b}$ is selected from —F, —Cl, and —Br, and each of $R^{3a}$ and $R^{3c}$ is hydrogen. In yet a further aspect, $R^{3b}$ is —F and each of $R^{3a}$ and $R^{3c}$ is hydrogen.

In a further aspect, $R^{3c}$ is halogen. In a still further aspect, $R^{3c}$ is selected from —F, —Cl, and —Br. In yet a further aspect, $R^{3c}$ is —F.

In a further aspect, $R^{3c}$ is halogen and each of $R^{3a}$ and $R^{3b}$ is hydrogen. In a still further aspect, $R^{3c}$ is selected from —F, —Cl, and —Br, and each of $R^{3a}$ and $R^{3b}$ is hydrogen. In yet a further aspect, $R^{3c}$ is —F and each of $R^{3a}$ and $R^{3b}$ is hydrogen.

d. $R^4$ Groups

In one aspect, $R^4$ is selected from hydrogen, halogen, —CN, SO$_2$NH$_2$, SO$_2$CH$_3$, SO$_2$CF$_3$, and NO$_2$. In a further aspect, $R^4$ is hydrogen.

In a further aspect, $R^4$ is selected from —CN, SO$_2$NH$_2$, SO$_2$CH$_3$, SO$_2$CF$_3$, and NO$_2$. In a still further aspect, $R^4$ is selected from —CN, SO$_2$NH$_2$, SO$_2$CH$_3$, and SO$_2$CF$_3$. In yet a further aspect, $R^4$ is selected from —CN, SO$_2$NH$_2$, and SO$_2$CH$_3$. In an even further aspect, $R^4$ is selected from —CN and SO$_2$NH$_2$. In a still further aspect, $R^4$ is NO$_2$. In yet a further aspect, $R^4$ is SO$_2$CF$_3$. In an even further aspect, $R^4$ is SO$_2$CH$_3$. In a still further aspect, $R^4$ is SO$_2$NH$_2$. In yet a further aspect, $R^4$ is —CN.

In a further aspect, $R^4$ is selected from hydrogen and halogen. In a still further aspect, $R^4$ is selected from hydrogen, —F, —Cl, and —Br. In yet a further aspect, $R^4$ is selected from hydrogen, —F, and —Cl. In an even further aspect, $R^4$ is selected from hydrogen and —I. In a still further aspect, $R^4$ is selected from hydrogen and —Br. In yet a further aspect, $R^4$ is selected from hydrogen and —Cl. In an even further aspect, $R^4$ is selected from hydrogen and —F.

In a further aspect, $R^4$ is halogen. In a still further aspect, $R^4$ is selected from —F, —Cl, and —Br. In yet a further aspect, $R^4$ is selected from —F and —Cl. In an even further aspect, $R^4$ is —I. In a still further aspect, $R^4$ is —Br. In yet a further aspect, $R^4$ is —Cl. In an even further aspect, $R^4$ is —F.

2. Example Compounds

In one aspect, a compound can be present as one or more of the following structures:

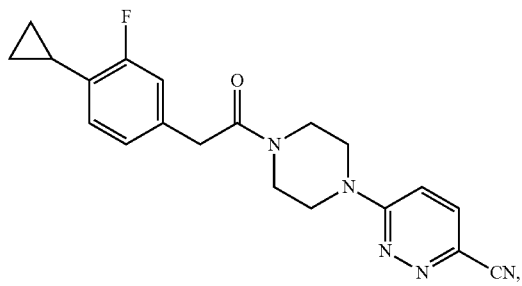

or a pharmaceutically acceptable salt thereof.

In a further aspect, a compound can be present as one or more of the following structures:

or a pharmaceutically acceptable salt thereof

3. Prophetic Compound Examples

The following compound examples are prophetic, and can be prepared using the synthesis methods described herein above and other general methods as needed as would be known to one skilled in the art. It is anticipated that the prophetic compounds would be active as PanK antagonists, and such activity can be determined using the assay methods described herein.
In one aspect, a compound can be selected from:
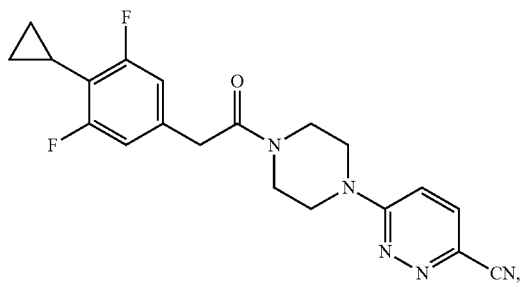
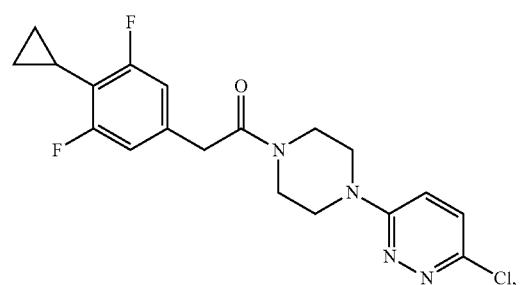
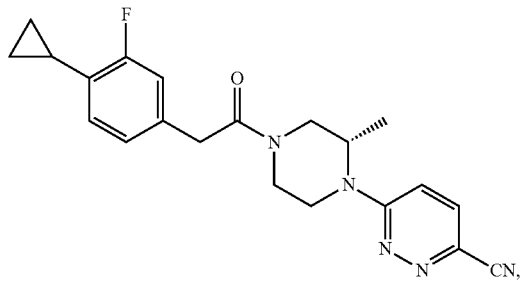
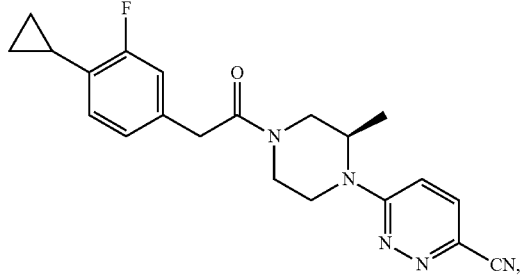
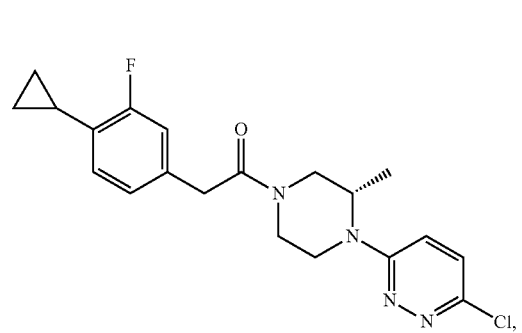
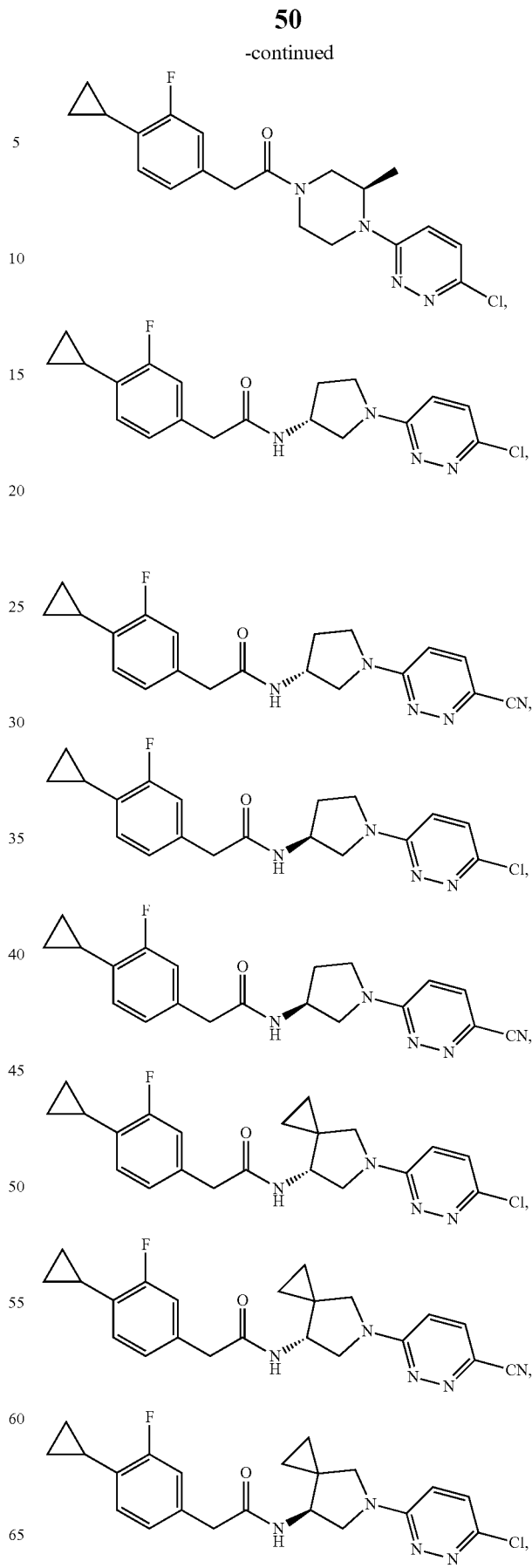

51
-continued
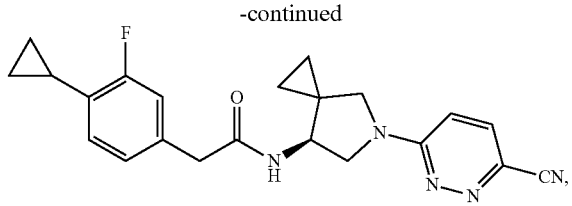
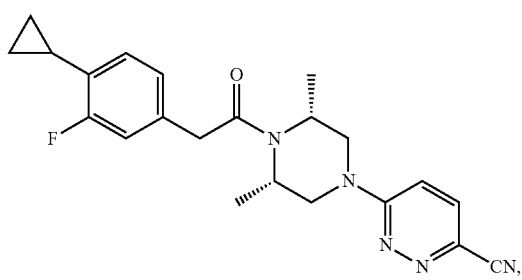
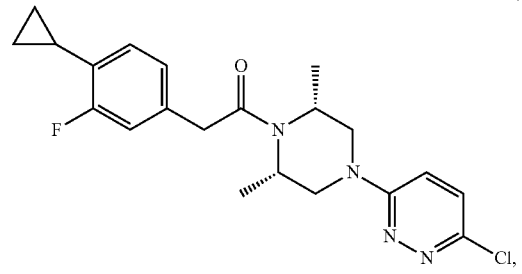
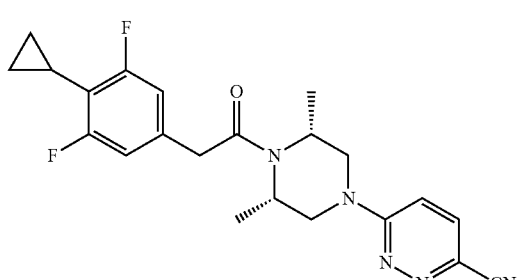
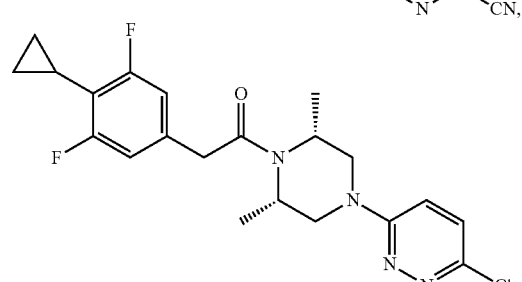
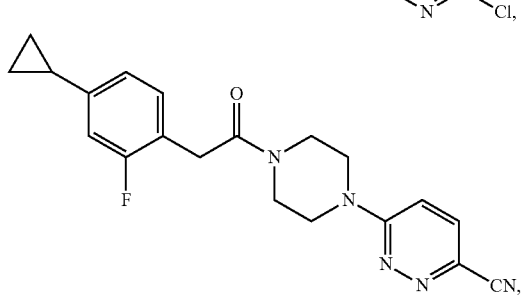
52
-continued
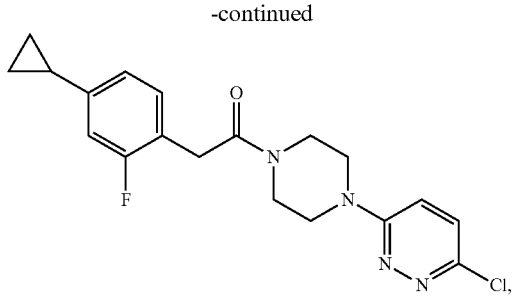
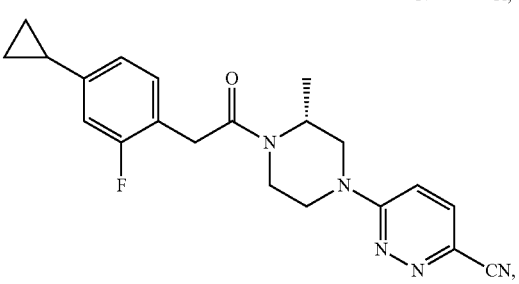
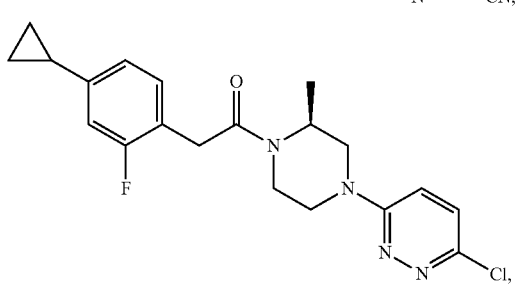
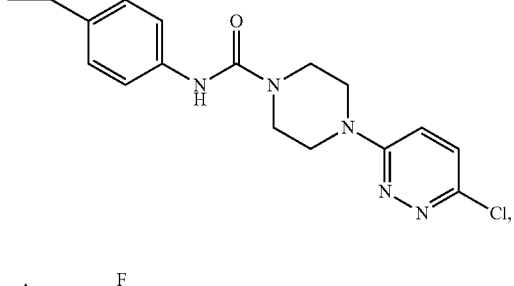
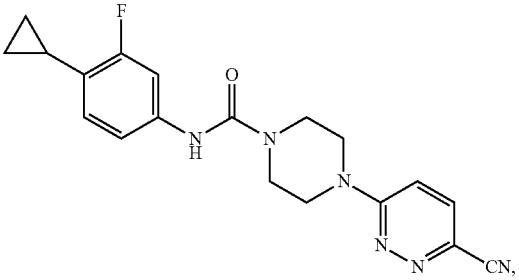
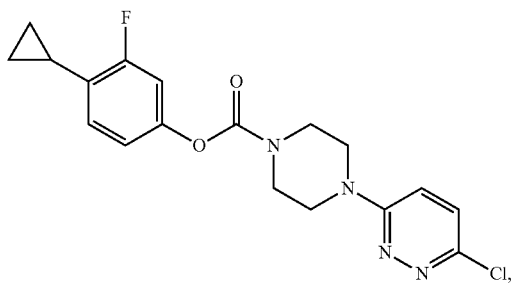

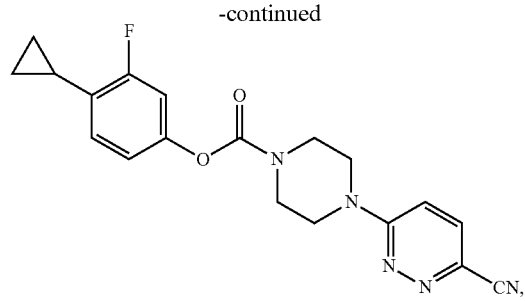

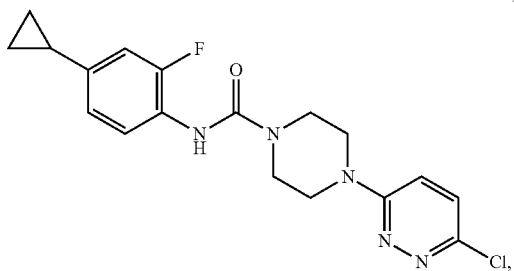

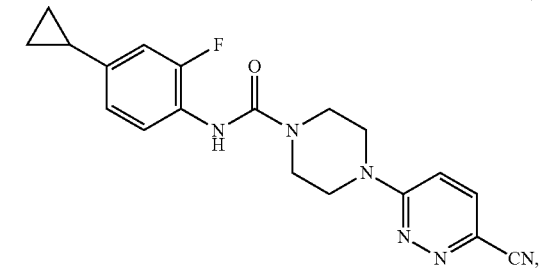

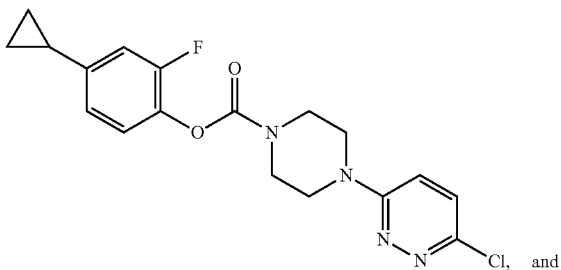

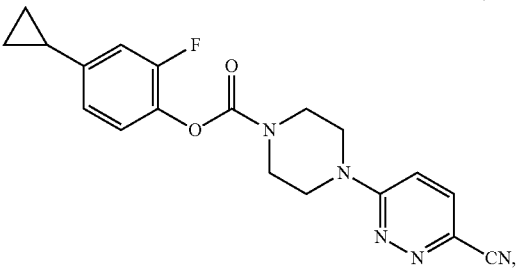

or a pharmaceutically acceptable derivative thereof.

C. METHODS OF MAKING A COMPOUND

The compounds of this invention can be prepared by employing reactions as shown in the following schemes, in addition to other standard manipulations that are known in the literature, exemplified in the experimental sections or clear to one skilled in the art. For clarity, examples having a single substituent are shown where multiple substituents are allowed under the definitions disclosed herein.

Reactions used to generate the compounds of this invention are prepared by employing reactions as shown in the following Reaction Schemes, as described and exemplified below. In certain specific examples, the disclosed compounds can be prepared by Routes I-VI, as described and exemplified below. The following examples are provided so that the invention might be more fully understood, are illustrative only, and should not be construed as limiting.

1. Route I

In one aspect, substituted small molecule modulators of PanK can be prepared as shown below.

SCHEME 1A.

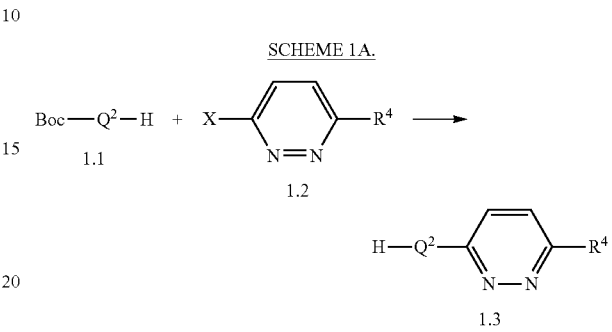

Compounds are represented in generic form, with substituents as noted in compound descriptions elsewhere herein; wherein X is halogen. A more specific example is set forth below.

SCHEME 1B.

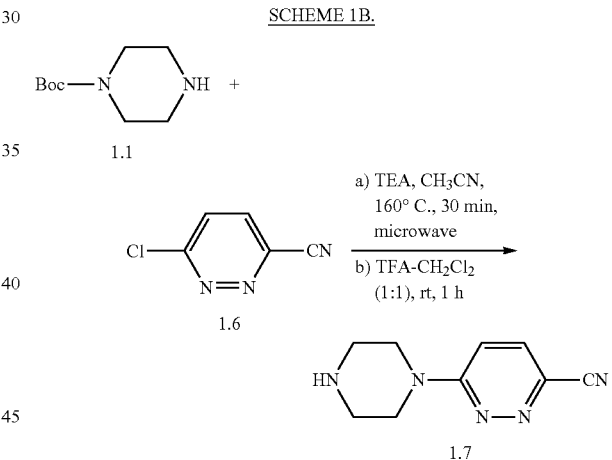

In one aspect, compounds of type 1.7, and similar compounds, can be prepared according to reaction Scheme 1B above. Thus, compounds of type 1.7 are either commercially available or can be prepared by an arylation reaction of an appropriate amine, e.g., 1.1 as shown above, and an appropriate aryl halide, e.g., 1.6 as shown above. Appropriate amines and appropriate aryl halides are commercially available or prepared by methods known to one skilled in the art. The arylation reaction is carried out in the presence of an appropriate base, e.g., triethylamine (TEA), in an appropriate solvent, e.g., acetonitrile, at an appropriate temperature, e.g., 160° C., for an appropriate period of time, e.g., 30 minutes using microwave irradiation. The arylation reaction is followed by a deprotection. The deprotection is carried out in the presence of an appropriate deprotecting agent, e.g., trifluoroacetic acid (TFA), in an appropriate solvent, e.g., dichloromethane, for an appropriate period of time, e.g., 1 hour. As can be appreciated by one skilled in the art, the above reaction provides an example of a generalized approach wherein compounds similar in structure to the specific reactants above (compounds similar to compounds of type 1.1 and 1.2), can be substituted in the reaction to provide substituted small molecule modulators of PanK similar to Formula 1.3.

2. Route II

In one aspect, substituted small molecule modulators of PanK can be prepared as shown below.

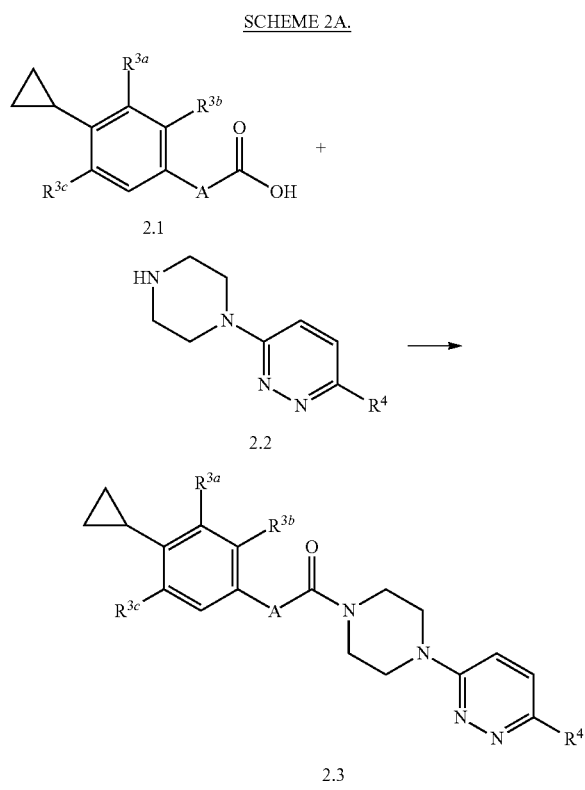

Compounds are represented in generic form, with substituents as noted in compound descriptions elsewhere herein and wherein A is selected from CH$_2$, CF$_2$, and CH(OH). A more specific example is set forth below.

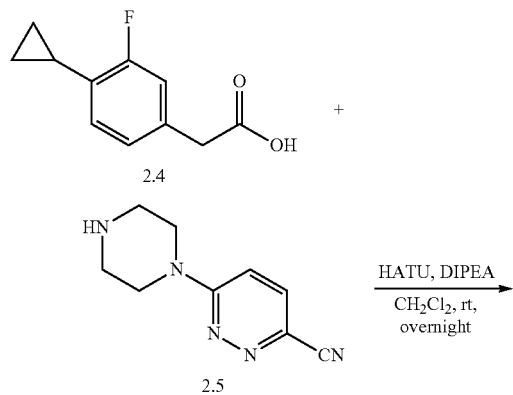

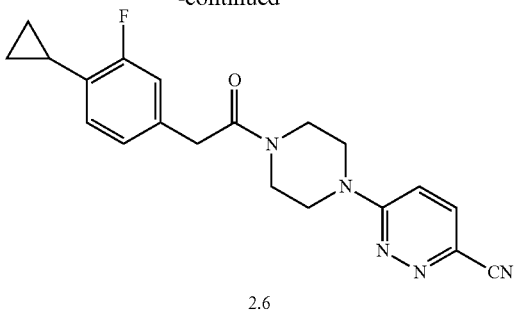

In one aspect, compounds of type 2.6, and similar compounds, can be prepared according to reaction Scheme 2B above. Thus, compounds of type 2.6 can be prepared by a coupling reaction of an appropriate carboxylic acid, e.g., 2.4 as shown above, with an appropriate amine, e.g., 2.5 as shown above. Appropriate carboxylic acids and appropriate amines are commercially available or prepared by methods known to one skilled in the art. The coupling reaction is carried out in the presence of an appropriate coupling agent, e.g., 1-[bis(dimethylamino)methylene]-1H-1,2,3-triazolo[4,5-b]pyridinium 3-oxid hexafluorophosphate (HATU), and an appropriate base, e.g., diisopropylethylamine (DIPEA), in an appropriate solvent, e.g., dichloromethane. As can be appreciated by one skilled in the art, the above reaction provides an example of a generalized approach wherein compounds similar in structure to the specific reactants above (compounds similar to compounds of type 2.1 and 2.2), can be substituted in the reaction to provide substituted small molecule modulators of PanK similar to Formula 2.3.

3. Route III

In one aspect, substituted small molecule modulators of PanK can be prepared as shown below.

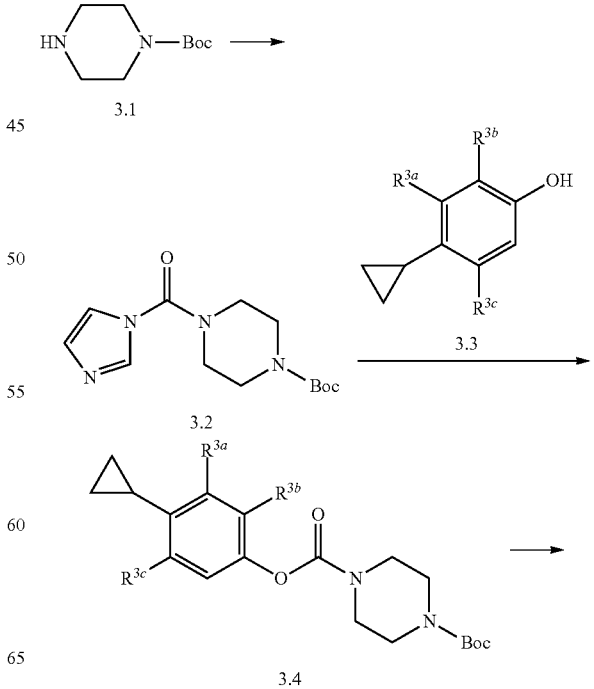

-continued

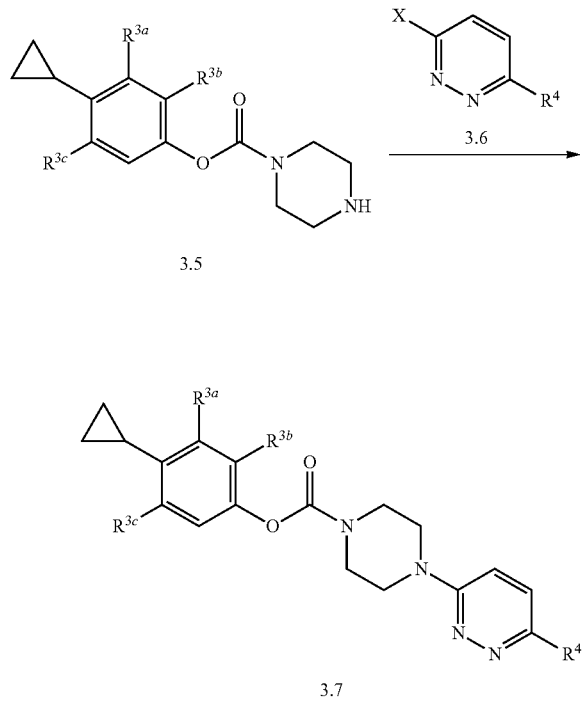

Compounds are represented in generic form, with substituents as noted in compound descriptions elsewhere herein and wherein X is halogen. A more specific example is set forth below.

SCHEME 3B

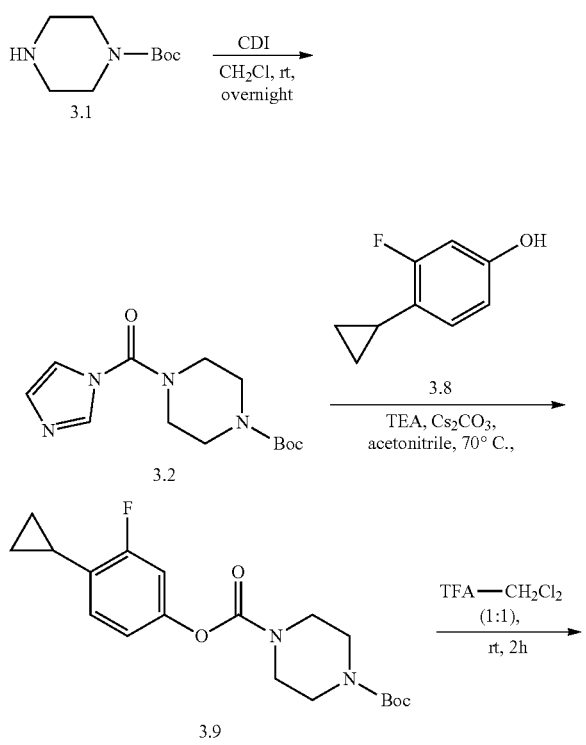

-continued

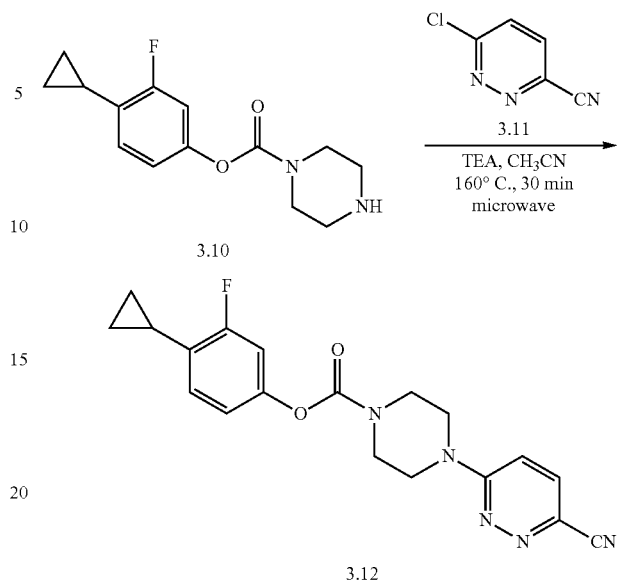

In one aspect, compounds of type 3.12, and similar compounds, can be prepared according to reaction Scheme 3B above. Thus, compounds of type 3.2 can be prepared by a coupling reaction of an appropriate amine, e.g., 3.1 as shown above. Appropriate amines are commercially available or prepared by methods known to one skilled in the art. The coupling reaction is carried out in the presence of an appropriate coupling agent, e.g., N,N-carbonyldiimidazole (CDI), in an appropriate solvent, e.g., dichloromethane. Compounds of type 3.9 can be prepared by a reaction of an appropriate activated-urea, e.g., 3.2, and an appropriate phenol, e.g., 3.8 as shown above. Appropriate phenols are commercially available or prepared by methods known to one skilled in the art. The reaction is carried out in the presence of an appropriate base, e.g., triethylamine and cesium carbonate, in an appropriate solvent, e.g., acetonitrile, at an appropriate temperature, e.g., 70° C., for an appropriate period of time, e.g., 3-4 hours or overnight. Compounds of type 3.10 can be prepared by a deprotection reaction of an appropriate piperazine, e.g., 3.9 as shown above. The deprotection reaction is carried out in the presence of an appropriate deprotecting agent, e.g., trifluoroacetic acid, and an appropriate solvent, e.g., dichloromethane, for an appropriate period of time, e.g., 2 hours. Compounds of type 3.12 can be prepared by an arylation reaction of an appropriate amine, e.g., 3.10 as shown above, and an appropriate aryl halide, e.g., 3.11 as shown above. Appropriate aryl halides are commercially available or prepared by methods known to one skilled in the art. The arylation reaction is carried out in the presence of an appropriate base, e.g., triethylamine, and an appropriate solvent, e.g., acetonitrile, at an appropriate temperature, e.g., 160° C., for an appropriate period of time, e.g., 30 minutes using microwave irradiations. As can be appreciated by one skilled in the art, the above reaction provides an example of a generalized approach wherein compounds similar in structure to the specific reactants above (compounds similar to compounds of type 3.1, 3.2, 3.3, 3.4, 3.5, and 3.6), can be substituted in the reaction to provide substituted small molecule modulators of PanK similar to Formula 3.7.

4. Route IV

In one aspect, substituted small molecule modulators of PanK can be prepared as shown below.

SCHEME 4A.

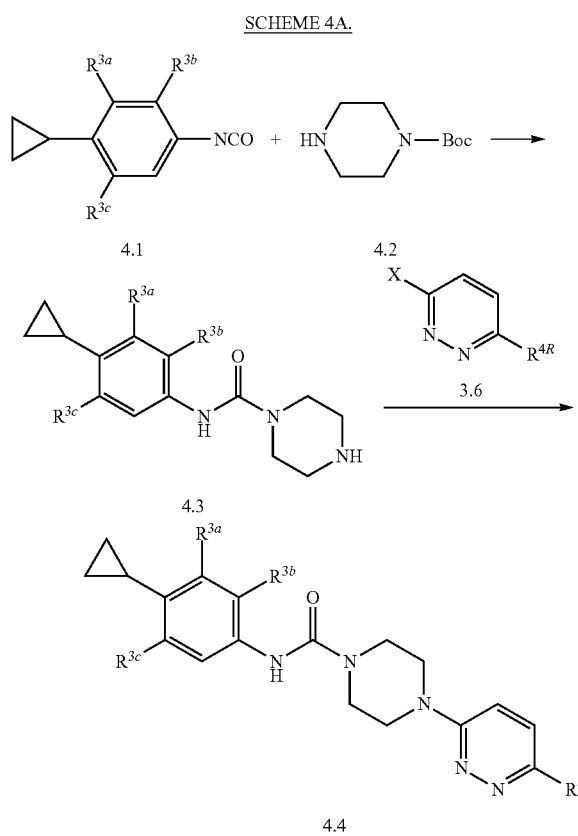

Compounds are represented in generic form, with substituents as noted in compound descriptions elsewhere herein and wherein X is halogen. A more specific example is set forth below.

SCHEME 4B.

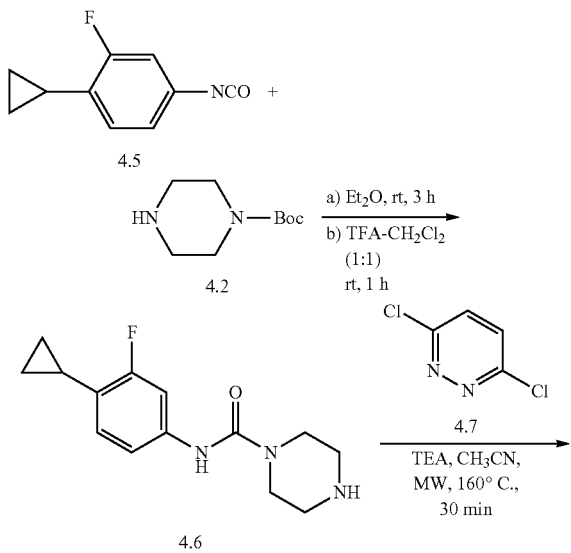

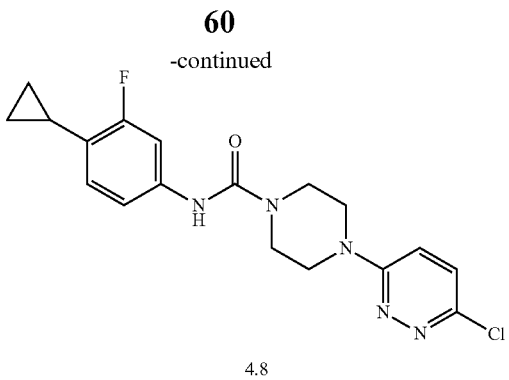

In one aspect, compounds of type 4.8, and similar compounds, can be prepared according to reaction Scheme 4B above. Thus, compounds of type 4.6 can be prepared by a urea bond formation reaction between an appropriate amine, e.g., 4.2 as shown above, and an appropriate isocyanate, e.g., 4.5 as shown above. Appropriate amines and appropriate isocyanates are commercially available or prepared by methods known to one skilled in the art. The nucleophilic substitution is carried out in the presence of an appropriate solvent, e.g., diethyl ether, for an appropriate period of time, e.g., 3 hours. The nucleophilic substitution is followed by a deprotection reaction. The deprotection reaction is carried out in the presence of an appropriate deprotecting agent, e.g., trifluoroacetic acid, in an appropriate solvent, e.g., dichloromethane, for an appropriate period of time, e.g., 1 hour. Compounds of type 4.8 can be prepared by an arylation reaction of appropriate amine, e.g., 4.6 as shown above, and an appropriate aryl halide, e.g., 4.7 as shown above. Appropriate aryl halides are commercially available or prepared by methods known to one skilled in the art. The arylation reaction is carried out in the presence of an appropriate base, e.g., triethylamine, in an appropriate solvent, e.g., acetonitrile, at an appropriate temperature, e.g, 160° C., for an appropriate period of time, e.g., 30 minutes using microwave irradiations. As can be appreciated by one skilled in the art, the above reaction provides an example of a generalized approach wherein compounds similar in structure to the specific reactants above (compounds similar to compounds of type 3.6, 4.1, 4.2, and 4.3), can be substituted in the reaction to provide 4-aryl-N-phenylpiperazine-1-carboxamide derivatives similar to Formula 4.4.

5. Route V

In one aspect, substituted small molecule modulators of PanK can be prepared as shown below.

SCHEME 5A.

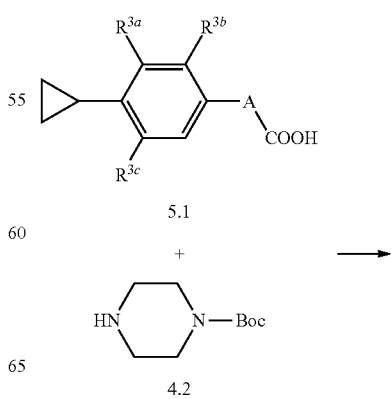

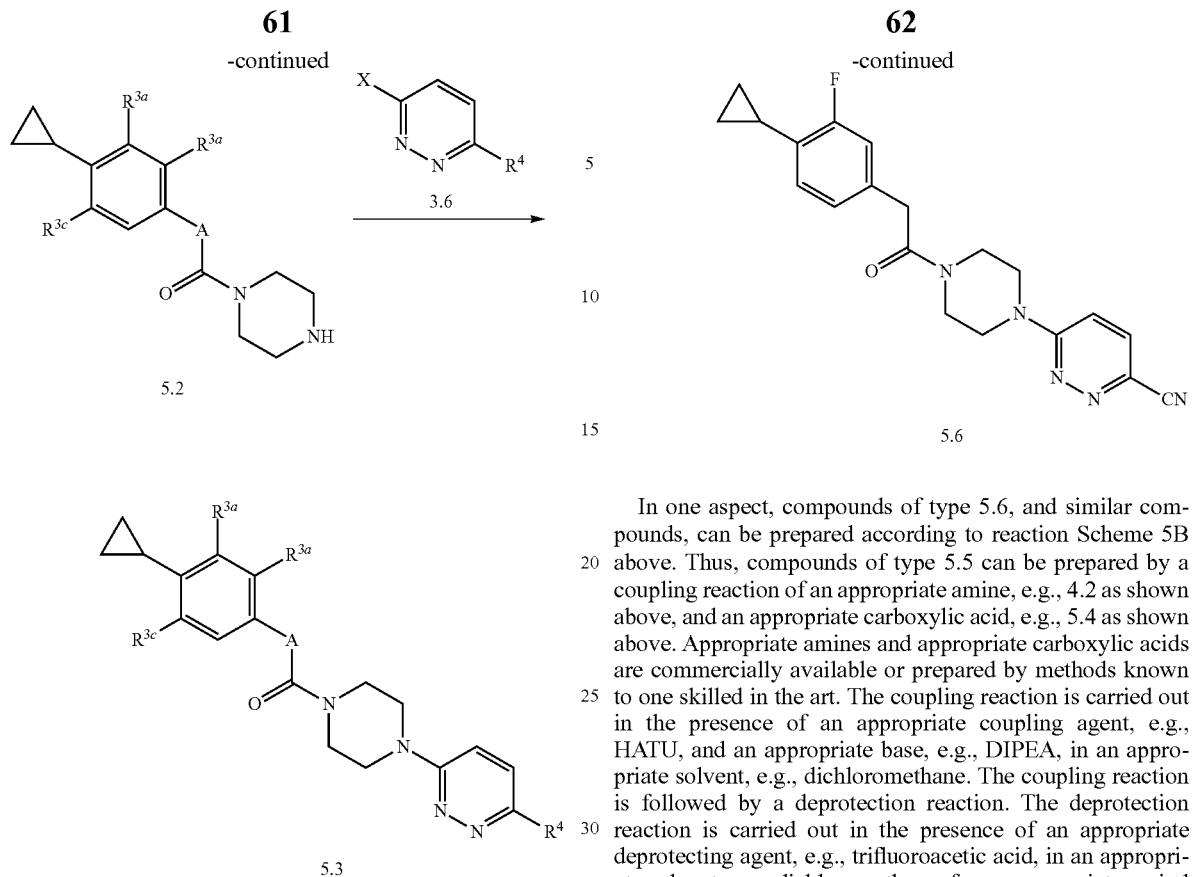

5.2

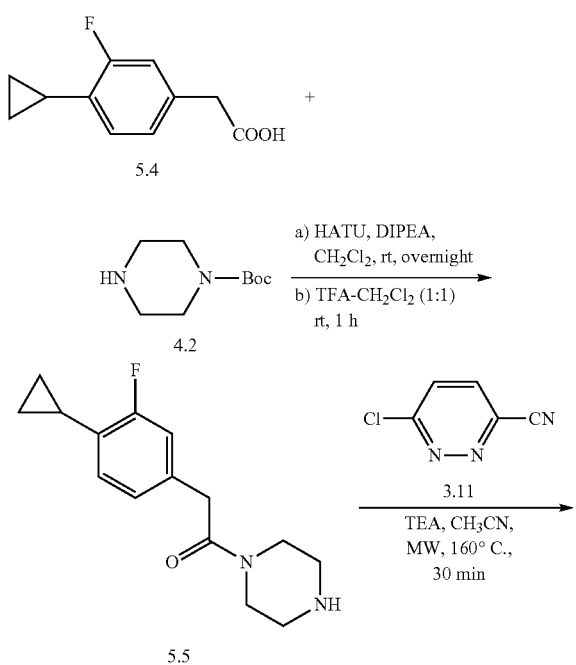

5.3

Compounds are represented in generic form, with substituents as noted in compound descriptions elsewhere herein and wherein X is halogen. A more specific example is set forth below.

SCHEME 5B.

5.6

In one aspect, compounds of type 5.6, and similar compounds, can be prepared according to reaction Scheme 5B above. Thus, compounds of type 5.5 can be prepared by a coupling reaction of an appropriate amine, e.g., 4.2 as shown above, and an appropriate carboxylic acid, e.g., 5.4 as shown above. Appropriate amines and appropriate carboxylic acids are commercially available or prepared by methods known to one skilled in the art. The coupling reaction is carried out in the presence of an appropriate coupling agent, e.g., HATU, and an appropriate base, e.g., DIPEA, in an appropriate solvent, e.g., dichloromethane. The coupling reaction is followed by a deprotection reaction. The deprotection reaction is carried out in the presence of an appropriate deprotecting agent, e.g., trifluoroacetic acid, in an appropriate solvent, e.g., dichloromethane, for an appropriate period of time, e.g., 1 hour. Compounds of type 5.6 can be prepared by an arylation reaction of an appropriate amine, e.g., 5.5, and an appropriate aryl halide, e.g., 3.11 as shown above. Appropriate aryl halides are commercially available or prepared by methods known to one skilled in the art. The arylation reaction is carried out in the presence of an appropriate base, e.g., triethylamine, in an appropriate solvent, e.g., acetonitrile, at an appropriate temperature, e.g., 160° C., for an appropriate period of time, e.g., 30 minutes using microwave irradiations. As can be appreciated by one skilled in the art, the above reaction provides an example of a generalized approach wherein compounds similar in structure to the specific reactants above (compounds similar to compounds of type 3.6, 4.2, 5.1, and 5.2), can be substituted in the reaction to provide substituted small molecule modulators of PanK similar to Formula 5.3.

It is contemplated that each disclosed method can further comprise additional steps, manipulations, and/or components. It is also contemplated that any one or more step, manipulation, and/or component can be optionally omitted from the invention. It is understood that a disclosed method can be used to provide the disclosed compounds. It is also understood that the products of the disclosed methods can be employed in the disclosed methods of using.

D. PHARMACEUTICAL COMPOSITIONS

In one aspect, disclosed are pharmaceutical compositions comprising a disclosed compound, or a pharmaceutically acceptable salt thereof and a pharmaceutically acceptable carrier.

In various aspects, the compounds and compositions of the invention can be administered in pharmaceutical compositions, which are formulated according to the intended method of administration. The compounds and compositions described herein can be formulated in a conventional manner using one or more physiologically acceptable carriers or excipients. For example, a pharmaceutical composition can be formulated for local or systemic administration, e.g., administration by drops or injection into the ear, insufflation (such as into the ear), intravenous, topical, or oral administration.

The nature of the pharmaceutical compositions for administration is dependent on the mode of administration and can readily be determined by one of ordinary skill in the art. In various aspects, the pharmaceutical composition is sterile or sterilizable. The therapeutic compositions featured in the invention can contain carriers or excipients, many of which are known to skilled artisans. Excipients that can be used include buffers (for example, citrate buffer, phosphate buffer, acetate buffer, and bicarbonate buffer), amino acids, urea, alcohols, ascorbic acid, phospholipids, polypeptides (for example, serum albumin), EDTA, sodium chloride, liposomes, mannitol, sorbitol, water, and glycerol. The nucleic acids, polypeptides, small molecules, and other modulatory compounds featured in the invention can be administered by any standard route of administration. For example, administration can be parenteral, intravenous, subcutaneous, or oral. A modulatory compound can be formulated in various ways, according to the corresponding route of administration. For example, liquid solutions can be made for administration by drops into the ear, for injection, or for ingestion; gels or powders can be made for ingestion or topical application. Methods for making such formulations are well known and can be found in, for example, Remington's Pharmaceutical Sciences, 18th Ed., Gennaro, ed., Mack Publishing Co., Easton, Pa. 1990.

In various aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

In various aspects, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In a further aspect, an effective amount is a therapeutically effective amount. In a still further aspect, an effective amount is a prophylactically effective amount.

In a further aspect, the pharmaceutical composition is administered to a mammal. In a still further aspect, the mammal is a human. In an even further aspect, the human is a patient.

In a further aspect, the pharmaceutical composition is used to treat a disorder associated with pantothenate kinase activity such as, for example, PKAN and diabetes.

It is understood that the disclosed compositions can be prepared from the disclosed compounds. It is also understood that the disclosed compositions can be employed in the disclosed methods of using.

E. METHODS OF TREATING A DISORDER ASSOCIATED WITH PANK ACTIVITY

In various aspects, the compounds and compositions disclosed herein are useful for treating, preventing, ameliorating, controlling or reducing the risk of a variety of disorders associated with pantothenate kinase activity, including, for example, PKAN, aging and diabetes. Thus, in one aspect, disclosed are methods of treating a disorder associated with pantothenate kinase activity in a subject, the method comprising administering to the subject an effective amount of at least one disclosed compound or a pharmaceutically acceptable salt thereof.

In various aspects, the disclosed compounds can be used in combination with one or more other drugs in the treatment, prevention, control, amelioration, or reduction of risk of disorders associated with PanK activity for which disclosed compounds or the other drugs can have utility, where the combination of the drugs together are safer or more effective than either drug alone. Such other drug(s) can be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and a disclosed compound is preferred. However, the combination therapy can also include therapies in which a disclosed compound and one or more other drugs are administered on different overlapping schedules. It is also contemplated that when used in combination with one or more other active ingredients, the disclosed compounds and the other active ingredients can be used in lower doses than when each is used singly. Accordingly, the pharmaceutical compositions include those that contain one or more other active ingredients, in addition to a compound of the present invention.

In a further aspect, the compound exhibits inhibition of PanK activity. In a still further aspect, the compound exhibits a decrease in PanK activity.

In a further aspect, the compound exhibits inhibition of PanK activity with an $IC_{50}$ of from about 0.001 µM to about 25 µM. In a still further aspect, the compound exhibits inhibition of PanK activity with an $IC_{50}$ of from about 0.001 µM to about 15 µM. In yet a further aspect, the compound exhibits inhibition of PanK activity with an $IC_{50}$ of from about 0.001 µM to about 10 µM. In an even further aspect, the compound exhibits inhibition of PanK activity with an $IC_{50}$ of from about 0.001 µM to about 5 µM. In a still further aspect, the compound exhibits inhibition of PanK activity with an $IC_{50}$ of from about 0.001 µM to about 1 µM. In yet a further aspect, the compound exhibits inhibition of PanK activity with an $IC_{50}$ of from about 0.001 µM to about 0.5 µM. In an even further aspect, the compound exhibits inhibition of PanK activity with an $IC_{50}$ of from about 0.001 µM to about 0.1 µM. In a still further aspect, the compound exhibits inhibition of PanK activity with an $IC_{50}$ of from about 0.001 µM to about 0.05 µM. In yet a further aspect, the compound exhibits inhibition of PanK activity with an $IC_{50}$ of from about 0.001 µM to about 0.01 µM. In an even further aspect, the compound exhibits inhibition of PanK activity with an $IC_{50}$ of from about 0.001 µM to about 0.005 µM. In a still further aspect, the compound exhibits inhibition of PanK activity with an $IC_{50}$ of from about 0.005 µM to about 25 µM. In yet a further aspect, the compound exhibits inhibition of PanK activity with an $IC_{50}$ of from about 0.01 µM to about 25 µM. In an even further aspect, the compound exhibits inhibition of PanK activity with an $IC_{50}$ of from about 0.05 µM to about 25 µM. In a still further aspect, the compound exhibits inhibition of PanK activity with an $IC_{50}$ of from about 0.1 µM to about 25 µM. In yet a further aspect, the compound exhibits inhibition of PanK activity with an $IC_{50}$ of from about 0.5 µM to about 25 µM. In an even further aspect, the compound exhibits inhibition of PanK activity with an $IC_{50}$ of from about 1 µM to about 25 µM. In a still further aspect, the compound exhibits inhibition of PanK activity with an $IC_{50}$ of from about 5 µM to about 25 µM. In yet a further aspect, the compound exhibits inhibition of PanK activity with an $IC_{50}$ of from about 10 µM to about 25 µM. In an even further aspect, the compound exhibits inhibition of PanK activity with an $IC_{50}$ of from about 15 µM to about 25 µM.

In a further aspect, the subject is a mammal. In a still further aspect, the mammal is human.

In a further aspect, the subject has been diagnosed with a need for treatment of the disorder prior to the administering step. In a still further aspect, the subject is at risk for developing the disorder prior to the administering step.

In a further aspect, the method further comprises identifying a subject at risk for developing the disorder prior to the administering step.

F. METHODS OF MODULATING PANK ACTIVITY IN AT LEAST ONE CELL

In one aspect, disclosed are methods of modulating pantothenate kinase activity in at least one cell, the method comprising the step of contacting the at least one cell with an effective amount of at least one disclosed compound, or a pharmaceutically acceptable salt thereof. In a further aspect, modulating is inhibiting.

In a further aspect, the cell is mammalian. In a still further aspect, the cell is human. In yet a further aspect, the cell has been isolated from a mammal prior to the contacting step.

In a further aspect, contacting is via administration to a mammal.

G. METHODS OF USING THE COMPOSITIONS

Provided are methods of using of a disclosed composition or medicament. In one aspect, the method of use is directed to the treatment of a disorder. In a further aspect, the disclosed compounds can be used as single agents or in combination with one or more other drugs in the treatment, prevention, control, amelioration, or reduction of risk of the aforementioned diseases, disorders and conditions for which the compound or the other drugs have utility, where the combination of drugs together are safer or more effective than either drug alone. The other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound can be more efficacious than either as a single agent.

The pharmaceutical compositions and methods of the present invention can further comprise other therapeutically active compounds as noted herein which are usually applied in the treatment of the above mentioned pathological conditions.

1. Manufacture of a Medicament

In one aspect, the invention relates to a method for the manufacture of a medicament for treating a disorder associated with PanK dysfunction in a mammal, the method comprising combining a therapeutically effective amount of a disclosed compound or product of a disclosed method with a pharmaceutically acceptable carrier or diluent.

As regards these applications, the present method includes the administration to an animal, particularly a mammal, and more particularly a human, of a therapeutically effective amount of the compound effective in the inhibition of protein and especially PanK. The dose administered to an animal, particularly a human, in the context of the present invention should be sufficient to affect a therapeutic response in the animal over a reasonable time frame. One skilled in the art will recognize that dosage will depend upon a variety of factors including the condition of the animal, the body weight of the animal, as well as the severity and stage of the disorder.

Thus, in one aspect, the invention relates to the manufacture of a medicament comprising combining a disclosed compound or a product of a disclosed method of making, or a pharmaceutically acceptable salt, solvate, or polymorph thereof, with a pharmaceutically acceptable carrier or diluent.

2. Use of Compounds and Compositions

Also provided are the uses of the disclosed compounds and compositions. Thus, in one aspect, the invention relates to the uses of modulators of PanK.

In a further aspect, the invention relates to the use of a disclosed compound or product of a disclosed method in the manufacture of a medicament for the treatment of a disorder associated with PanK activity and associated Coenzyme A levels such as, for example, PKAN and diabetes.

In a further aspect, the use relates to a process for preparing a pharmaceutical composition comprising a therapeutically effective amount of a disclosed compound or a product of a disclosed method, and a pharmaceutically acceptable carrier, for use as a medicament.

In a further aspect, the use relates to a process for preparing a pharmaceutical composition comprising a therapeutically effective amount of a disclosed compound or a product of a disclosed method, wherein a pharmaceutically acceptable carrier is intimately mixed with a therapeutically effective amount of the disclosed compound or the product of a disclosed method.

In various aspects, the use relates to the treatment of PKAN in a vertebrate animal. In a further aspect, the use relates to the treatment of PKAN in a human subject.

In a further aspect, the use is the treatment of diabetes. In a still further aspect, the diabetes is type II diabetes.

It is understood that the disclosed uses can be employed in connection with the disclosed compounds, methods, compositions, and kits. In a further aspect, the invention relates to the use of a disclosed compound or composition of a medicament for the treatment of a disorder associated with PanK activity in a mammal.

In a further aspect, the invention relates to the use of a disclosed compound or composition in the manufacture of a medicament for the treatment of a disorder associated with PanK activity selected from PKAN and diabetes.

3. Kits

In one aspect, disclosed are kits comprising a disclosed compound and one or more of: (a) at least one agent known to treat PKAN; (b) at least one agent known to treat diabetes; (c) instructions for treating PKAN; and (d) instructions for treating diabetes, metabolic syndrome, and/or side effects of aging.

In various aspects, the agents and pharmaceutical compositions described herein can be provided in a kit. The kit can also include combinations of the agents and pharmaceutical compositions described herein.

In various aspects, the informational material can be descriptive, instructional, marketing or other material that relates to the methods described herein and/or to the use of the agents for the methods described herein. For example, the informational material may relate to the use of the agents herein to treat a subject who has, or who is at risk for developing, a disorder associated with PanK activity. The kits can also include paraphernalia for administering the agents of this invention to a cell (in culture or in vivo) and/or for administering a cell to a patient.

In various aspects, the informational material can include instructions for administering the pharmaceutical composition and/or cell(s) in a suitable manner to treat a human, e.g., in a suitable dose, dosage form, or mode of administration (e.g., a dose, dosage form, or mode of administration described herein). In a further aspect, the informational material can include instructions to administer the pharmaceutical composition to a suitable subject, e.g., a human having, or at risk for developing, a disorder associated with PanK activity.

In various aspects, the composition of the kit can include other ingredients, such as a solvent or buffer, a stabilizer, a preservative, a fragrance or other cosmetic ingredient. In such aspects, the kit can include instructions for admixing the agent and the other ingredients, or for using one or more compounds together with the other ingredients.

In a further aspect, the compound and the at least one agent known to treat PKAN are co-formulated. In a still further aspect, the compound and the at least one agent known to treat PKAN are co-packaged.

In a further aspect, the compound and the at least one agent known to treat diabetes are co-formulated. In a still further aspect, the compound and the at least one agent known to treat diabetes are co-packaged.

In a further aspect, the at least one agent known to treat PKAN is selected from baclofen, trihexyphenidyl, botulinum toxin, and an iron chelating agent. In a still further aspect, the iron chelating agent is deferriprone.

In a further aspect, the kit further comprises a plurality of dosage forms, the plurality comprising one or more doses; wherein each dose comprises an effective amount of the compound and the at least one agent known to treat PKAN. In a still further aspect, the effective amount is a therapeutically effective amount. In yet a further aspect, the effective amount is a prophylactically effective amount. In an even further aspect, each dose of the compound and at least one agent known to treat PKAN are co-packaged. In a still further aspect, each dose of the compound and the at least one agent known to treat PKAN are co-formulated.

In a further aspect, the at least one agent known to treat diabetes is selected from insulin, albiglutide, exenatide, liraglutide, pramlintide, dulaglutide, acarbose, alogliptin, bromocriptine mesylate, canagliflozin, chlorpropamide, colesevelam, dapagliflozin, empagliflozin, glimepiride, glipizide, glyburide, linagliptin, metformin, miglitol, nateglinide, pioglitazone, repaglinide, rosiglitazone, saxagliptin, and sitagliptin.

In a further aspect, the kit further comprises a plurality of dosage forms, the plurality comprising one or more doses; wherein each dose comprises an effective amount of the compound and at least one agent known to treat diabetes. In a still further aspect, the effective amount is a therapeutically effective amount. In yet a further aspect, the effective amount is a prophylactically effective amount. In an even further aspect, each dose of the compound and at least one agent known to treat diabetes are co-packaged. In a still further aspect, each dose of the compound and at least one agent known to treat diabetes are co-formulated.

4. Subjects

In various aspects, the subject of the herein disclosed methods is a vertebrate, e.g., a mammal. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

In some aspects of the disclosed methods, the subject has been diagnosed with a need for treatment prior to the administering step. In some aspects of the disclosed method, the subject has been diagnosed with a disorder associated with PanK activity prior to the administering step. In some aspects of the disclosed methods, the subject has been identified with a need for treatment prior to the administering step. In one aspect, a subject can be treated prophylactically with a compound or composition disclosed herein, as discussed herein elsewhere.

a. Dosage

Toxicity and therapeutic efficacy of the agents and pharmaceutical compositions described herein can be determined by standard pharmaceutical procedures, using either cells in culture or experimental animals to determine the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio $LD_{50}/ED_{50}$. Polypeptides or other compounds that exhibit large therapeutic indices are preferred.

Data obtained from cell culture assays and further animal studies can be used in formulating a range of dosage for use in humans. The dosage of such compounds lies preferably within a range of circulating concentrations that include the $ED_{50}$ with little or no toxicity, and with little or no adverse effect on a human's ability to hear. The dosage may vary within this range depending upon the dosage form employed and the route of administration utilized. For any agents used in the methods described herein, the therapeutically effective dose can be estimated initially from cell culture assays. A dose can be formulated in animal models to achieve a circulating plasma concentration range that includes the $IC_{50}$ (that is, the concentration of the test compound which achieves a half-maximal inhibition of symptoms) as determined in cell culture. Such information can be used to more accurately determine useful doses in humans. Exemplary dosage amounts of a differentiation agent are at least from about 0.01 to 3000 mg per day, e.g., at least about 0.00001, 0.0001, 0.001, 0.01, 0.1, 1, 2, 5, 10, 25, 50, 100, 200, 500, 1000, 2000, or 3000 mg per kg per day, or more.

The formulations and routes of administration can be tailored to the disease or disorder being treated, and for the specific human being treated. For example, a subject can receive a dose of the agent once or twice or more daily for one week, one month, six months, one year, or more. The treatment can continue indefinitely, such as throughout the lifetime of the human. Treatment can be administered at regular or irregular intervals (once every other day or twice per week), and the dosage and timing of the administration can be adjusted throughout the course of the treatment. The dosage can remain constant over the course of the treatment regimen, or it can be decreased or increased over the course of the treatment.

In various aspects, the dosage facilitates an intended purpose for both prophylaxis and treatment without undesirable side effects, such as toxicity, irritation or allergic response. Although individual needs may vary, the determination of optimal ranges for effective amounts of formulations is within the skill of the art. Human doses can readily be extrapolated from animal studies (Katocs et al., (1990) Chapter 27 in Remington's Pharmaceutical Sciences, 18th Ed., Gennaro, ed., Mack Publishing Co., Easton, Pa.). In general, the dosage required to provide an effective amount of a formulation, which can be adjusted by one skilled in the art, will vary depending on several factors, including the age, health, physical condition, weight, type and extent of the disease or disorder of the recipient, frequency of treatment, the nature of concurrent therapy, if required, and the nature and scope of the desired effect(s) (Nies et al., (1996) Chapter 3, In: Goodman & Gilman's The Pharmacological Basis of Therapeutics, 9th Ed., Hardman et al., eds., McGraw-Hill, New York, NY).

b. Routes of Administration

Also provided are routes of administering the disclosed compounds and compositions. The compounds and compositions of the present invention can be administered by direct therapy using systemic administration and/or local administration. In various aspects, the route of administration can be determined by a patient's health care provider or clinician, for example following an evaluation of the patient. In various aspects, an individual patient's therapy may be customized, e.g., the type of agent used, the routes of administration, and the frequency of administration can be personalized. Alternatively, therapy may be performed using a standard course of treatment, e.g., using pre-selected agents and pre-selected routes of administration and frequency of administration.

Systemic routes of administration can include, but are not limited to, parenteral routes of administration, e.g., intravenous injection, intramuscular injection, and intraperitoneal injection; enteral routes of administration e.g., administration by the oral route, lozenges, compressed tablets, pills, tablets, capsules, drops (e.g., ear drops), syrups, suspensions and emulsions; rectal administration, e.g., a rectal suppository or enema; a vaginal suppository; a urethral suppository; transdermal routes of administration; and inhalation (e.g., nasal sprays).

In various aspects, the modes of administration described above may be combined in any order.

H. EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

The Examples are provided herein to illustrate the invention, and should not be construed as limiting the invention in any way. Examples are provided herein to illustrate the invention and should not be construed as limiting the invention in any way.

1. Chemistry Experimentals
A. General Synthesis Procedures
i. Method A: 6-(4-(2-(4-cyclopropyl-3-fluorophenyl)acetyl)piperazin-1-yl)pyridazine-3-carbonitrile To a cold (ice), stirred mixture of 2-(4-cyclopropyl-3-fluorophenyl)acetic acid (150 mg, 0.772 mmol), 4-(6-cyanopyridazin-3-yl)piperazin-1-ium chloride (218 mg, 0.850 mmol, 88%), and HATU (382 mg, 1.0 mmol) in DMF (3.0 mL) was added neat DIPA (404 µL, 2.32 mmol). The mixture was warmed to rt, stirred for 16 hours, and then heated at 50° C. for 1 hour. Next, the mixture was cooled to rt, diluted with water (10 mL), and extracted with ethyl acetate (2×15 mL). The combined extracts were washed with aq. 1N HCl, bicarbonate solution, and brine, dried over Na$_2$SO$_4$, and concentrated. The residue was purified on a 25 g SiO$_2$ cartridge using a gradient of ethyl acetate in hexanes (50% to 100%, and 100%) to afford the title compound (160 mg, 56.7%) as a beige solid. Rf=0.25 (EtOAc).

ii. Method B: 6-(4-(2-(4-cyclopropyl-3-fluorophenyl)acetyl)piperazin-1-yl)pyridazine-3-carbonitrile To a cold (ice), stirred mixture of 2-(4-cyclopropyl-3-fluorophenyl)acetic acid (3.35 g, 17.2 mmol) and 1-(6-cyanopyridazin-3-yl)piperazine-1,4-diium chloride (4.97 g, 19.0 mmol) in DMF (35 mL) was added a 50% solution of propylphosphonic anhydride (13.3 mL, 22.4 mmol) in DMF, followed by the addition of neat DIPA (13.8 mL, 79.3 mmol). The reaction mixture was slowly warmed to rt and stirred for 17 hours. Next, the reaction was slowly quenched with water (100 mL) (slightly exothermic) and stirred for 10 min before being filtered off using a Buchner funnel, washed with water (500 mL), and dried under high vacuum to afford 6-(4-(2-(4-cyclopropyl-3 fluorophenyl)acetyl)piperazin-1-yl)pyridazine-3-carbonitrile (5.95 g, 94.4%) as an off-white solid. The purity of this product is greater than 95%. The product (4.77 g) was added in a mixture of MeOH-EtOAc (1:1, 100 mL). The suspension was then heated at 80° C. for 10 min to reach a clear, pale yellow solution. The solution was filtered out and the filtrate was kept at room temperature for 24 hours. The solid was filtered, rinsed with EtOAc (10 mL), and dried to afford 6-(4-(2-(4-cyclopropyl-3-fluorophenypacetyppiperazin-1-yl)pyridazine-3-carbonitrile (3.65 g, 76.5%) as an off-white solid. HPLC purity, >99.9%.

b. Spectral Data of Exemplary Compounds i. Example 1: 6-(4-(2-(4-cyclopropyl-3-fluorophenyl)acetyl)piperazin-1-yl)pyridazine-3-carbonitrile

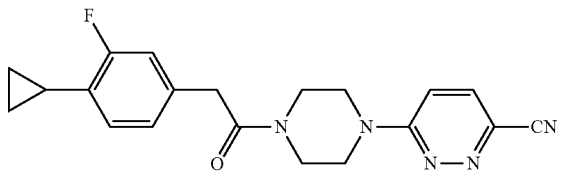 [SMILES: N#Cc1ccc(N2CCN(C(=O)Cc3ccc(C4CC4)c(F)c3)CC2)nn1]

$^1$H NMR (600 MHz, CDCl$_3$) δ 7.50 (d, J=9.6 Hz, 1H), 6.96-6.95 (m, 1H), 6.94 (s, 1H), 6.88 (t, J=7.9 Hz, 1H), 6.85 (d, J=9.6 Hz, 1H), 3.87-3.82 (m, 2H), 3.82-3.78 (m, 2H), 3.76 (s, 2H), 3.74-3.70 (m, 2H), 3.67-3.63 (m, 2H), 2.11-2.02 (m, 1H), 1.02-0.96 (m, 2H), 0.75-0.69 (m, 2H). $^{19}$F NMR (376 MHz, CDCl$_3$) δ −119.81 (dd, J=11.0, 7.9 Hz). LRMS, m/z: 388.07 (M+Na)+, 364.03 (M-1).

iii. Example 2: 1-(4-(6-chloropyridazin-3-yl)piperazin-1-yl)-2-(4-cyclopropyl-3-fluorophenyl)ethan-1-one

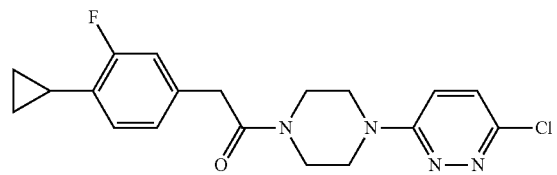 [SMILES: O=C(Cc1ccc(C2CC2)c(F)c1)N1CCN(c2ccc(Cl)nn2)CC1]

$^1$H NMR (500 MHz, Chloroform-d) δ 7.27 (d, J=14.5 Hz, 1H), 7.05-6.77 (m, 4H), 3.89-3.51 (m, 10H), 2.18-1.97 (m, 1H), 1.06-0.87 (m, 2H), 0.72 (dd, J=5.1, 1.8 Hz, 2H). ESI-MS (M+1): 375.52.

iv. Example 3: (S)-6-(4-(2-(4-cyclopropyl-3-fluorophenyl)acetyl)-3-methylpiperazin-1-yl)pyridazine-3-carbonitrile

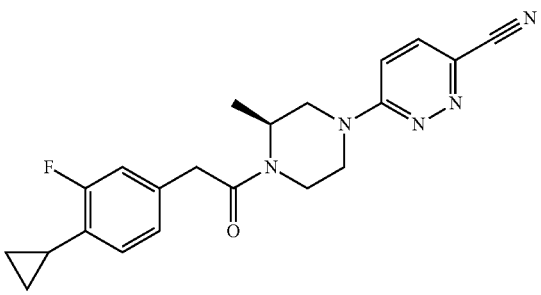 [SMILES: C[C@H]1CN(c2ccc(C#N)nn2)CCN1C(=O)Cc1ccc(C2CC2)c(F)c1]

$^1$H NMR (500 MHz, Chloroform-d) δ 7.40 (d, J=9.5 Hz, 1H), 6.96-6.66 (m, 4H), 4.95-4.46 (m, 1H), 4.44-3.91 (m, 3H), 3.64 (s, 2H), 3.47-2.90 (m, 3H), 2.05-1.91 (m, 2H), 1.16-1.05 (m, 3H), 0.90 (dd, J=8.3, 2.0 Hz, 2H), 0.63 (d, J=5.3 Hz, 2H). ESI-MS (M+1): 380.52.

v. Example 4: (R)-6-(4-(2-(4-cyclopropyl-3-fluorophenyl)acetyl)-3-methylpiperazin-1-yl)pyridazine-3-carbonitrile

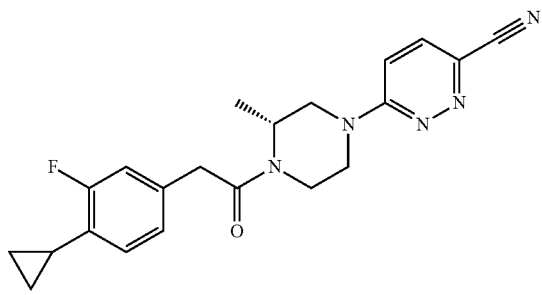 [SMILES: C[C@@H]1CN(c2ccc(C#N)nn2)CCN1C(=O)Cc1ccc(C2CC2)c(F)c1]

¹H NMR (500 MHz, Chloroform-d) δ 7.40 (d, J=9.4 Hz, 1H), 6.95-6.65 (m, 4H), 4.93-4.45 (m, 1H), 4.44-3.89 (m, 3H), 3.76-3.58 (m, 2H), 3.46-2.91 (m, 3H), 2.08-1.91 (m, 1H), 1.12 (d, J=6.6 Hz, 3H), 0.97-0.82 (m, 2H), 0.68-0.55 (m, 2H). ESI-MS (M+1): 380.52.

vi. Example 5: (R)-1-(4-(6-chloropyridazin-3-yl)-2-methylpiperazin-1-yl)-2-(4-cyclopropyl-3-fluorophenyl)ethan-1-one

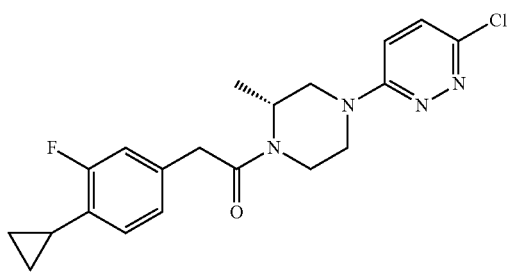 [SMILES: C[C@@H]1CN(c2ccc(Cl)nn2)CCN1C(=O)Cc1ccc(C2CC2)c(F)c1]

¹H NMR (500 MHz, Chloroform-d) δ 7.26-7.12 (m, 1H), 6.93-6.71 (m, 4H), 4.92-4.39 (m, 1H), 4.30-3.74 (m, 3H), 3.64 (s, 2H), 3.45-2.91 (m, 3H), 1.97 (td, J=8.4, 4.3 Hz, 1H), 1.18-1.08 (m, 3H), 0.95-0.82 (m, 2H), 0.69-0.53 (m, 2H). ESI-MS (M+1): 389.42.

vii. Example 6: (S)-1-(4-(6-chloropyridazin-3-yl)-2-methylpiperazin-1-yl)-2-(4-cyclopropyl-3-fluorophenyl)ethan-1-one

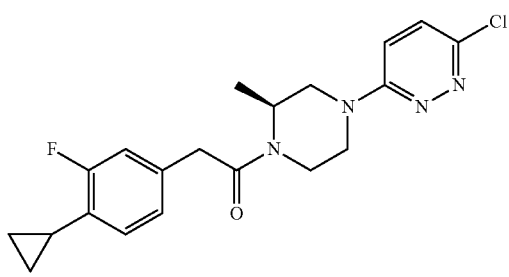 [SMILES: C[C@H]1CN(c2ccc(Cl)nn2)CCN1C(=O)Cc1ccc(C2CC2)c(F)c1]

¹H NMR (500 MHz, Chloroform-d) δ 7.24-7.09 (m, 1H), 6.92-6.63 (m, 4H), 4.95-4.40 (m, 1H), 4.31-3.74 (m, 3H), 3.64 (s, 2H), 3.44-3.15 (m, 1H), 3.15-2.75 (m, 2H), 2.03-1.91 (m, 1H), 1.17-1.06 (m, 3H), 0.95-0.83 (m, 2H), 0.63 (dd, J=5.2, 1.8 Hz, 2H). ESI-MS (M+1): 389.42.

viii. Example 7: 1-(4-(6-chloropyridazin-3-yl)piperazin-1-yl)-2-(4-cyclopropylphenyl)ethan-1-one

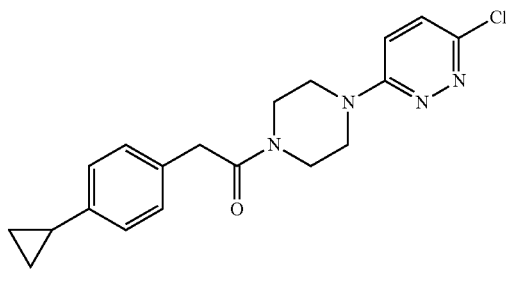 [SMILES: O=C(Cc1ccc(C2CC2)cc1)N1CCN(c2ccc(Cl)nn2)CC1]

¹H NMR (500 MHz, Chloroform-d) δ 7.31-7.11 (m, 1H), 7.07 (d, J=7.8 Hz, 2H), 6.95 (d, J=7.8 Hz, 2H), 6.81 (d, J=9.5 Hz, 1H), 3.86-3.27 (m, 8H), 1.88-1.74 (m, 1H), 0.96-0.77 (m, 2H), 0.59 (d, J=5.2 Hz, 2H). ESI-MS (M+1): 357.31.

ix. Example 8; (r)-6-(4-(2-(4-cyclopropylphenyl)acetyl)-3-methylpiperazin-1-yl)pyridazine-3-carbonitrile

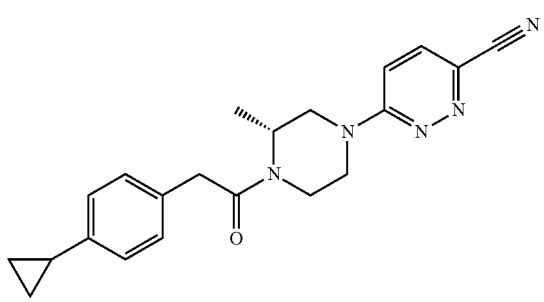 [SMILES: C[C@@H]1CN(c2ccc(C#N)nn2)CCN1C(=O)Cc1ccc(C2CC2)cc1]

¹H NMR (500 MHz, Chloroform-d) δ 7.38 (d, J=9.6 Hz, 1H), 7.05 (d, J=6.9 Hz, 2H), 6.95 (d, J=7.8 Hz, 2H), 6.78-6.63 (m, 1H), 4.97-4.45 (m, 1H), 4.38-3.91 (m, 2H), 3.79-3.59 (m, 3H), 3.45-2.98 (m, 3H), 1.79 (ddd, J=13.5, 8.7, 5.1 Hz, 1H), 1.10 (d, J=6.7 Hz, 3H), 0.94-0.81 (m, 2H), 0.66-0.53 (m, 2H). ESI-MS (M+1): 362.56.

x. Example 9; (s)-6-(4-(2-(4-cyclopropylphenyl)acetyl)-3-methylpiperazin-1-yl)pyridazine-3-carbonitrile

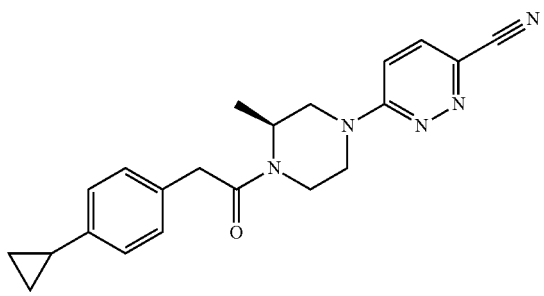 [SMILES: C[C@H]1CN(c2ccc(C#N)nn2)CCN1C(=O)Cc1ccc(C2CC2)cc1]

$^1$H NMR (500 MHz, Chloroform-d) δ 7.47 (d, J=9.6 Hz, 1H), 7.14 (d, J=6.9 Hz, 2H), 7.04 (d, J=7.7 Hz, 2H), 6.91-6.70 (m, 1H), 4.79 (dd, J=170.2, 10.0 Hz, 1H), 4.48-3.98 (m, 2H), 3.86-3.69 (m, 3H), 3.55-2.93 (m, 3H), 1.88 (tt, J=8.6, 5.0 Hz, 1H), 1.19 (d, J=6.7 Hz, 3H), 0.97 (dd, J=8.4, 2.1 Hz, 2H), 0.73-0.63 (m, 2H). ESI-MS (M+1): 362.47.

xi. Example 10; (r)-1-(4-(6-chloropyridazin-3-yl)-2-methylpiperazin-1-yl)-2-(4-cyclopropylphenyl)ethan-1-one

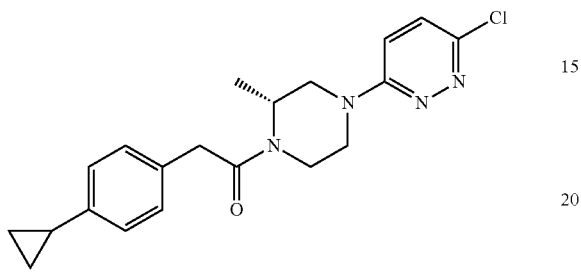

$^1$H NMR (500 MHz, DMSO-d$_6$) δ 7.53 (d, J=9.6 Hz, 1H), 7.38 (dt, J=14.5, 6.0 Hz, 1H), 7.11 (dd, J=12.5, 7.4 Hz, 2H), 7.01 (d, J=7.7 Hz, 2H), 4.71-4.20 (m, 2H), 4.18-4.05 (m, 2H), 3.92-3.56 (m, 3H), 3.26-2.80 (m, 2H), 1.88 (tt, J=8.5, 5.1 Hz, 1H), 1.05 (d, J=6.6 Hz, 3H), 0.92 (dd, J=8.5, 2.2 Hz, 2H), 0.70-0.56 (m, 2H). ESI-MS (M+1): 371.42.

2. Characterization of Exemplary Compounds

The compounds below in Table 1 were synthesized with methods identical or analogous to those described herein. The requisite starting materials were commercially available, described in the literature, or readily synthesized by one skilled in the art of organic synthesis.

TABLE 1

| No. | Structure | hPanK3 IC$_{50}$ (nM) |
| --- | --- | --- |
| 1 | 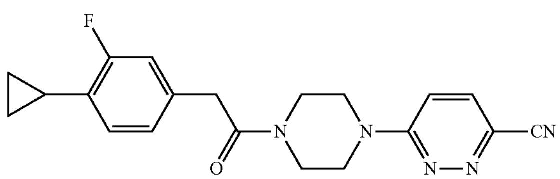 [SMILES: N#Cc1ccc(N2CCN(C(=O)Cc3ccc(C4CC4)c(F)c3)CC2)nn1] | 8.9 ± 0.8 |
| 2 | 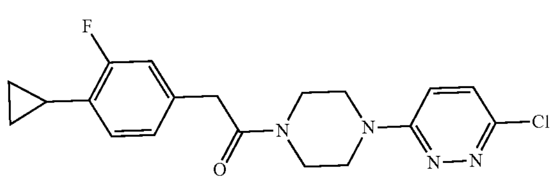 [SMILES: O=C(Cc1ccc(C2CC2)c(F)c1)N1CCN(c2ccc(Cl)nn2)CC1] | 2.9 ± 0.5 |
| 3 | 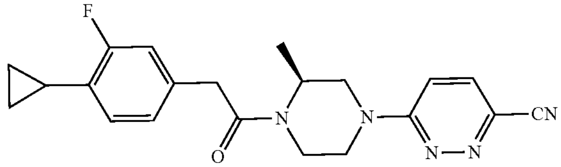 [SMILES: C[C@H]1CN(c2ccc(C#N)nn2)CCN1C(=O)Cc1ccc(C2CC2)c(F)c1] | 6.5 ± 0.8 |

TABLE 1-continued

| No. | Structure | hPanK3 IC$_{50}$ (nM) |
|---|---|---|
| 4 | 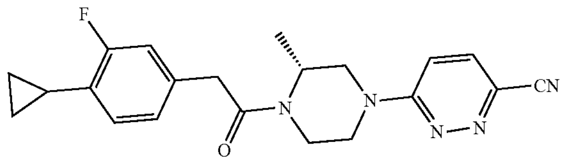 [SMILES: C[C@@H]1CN(c2ccc(C#N)nn2)CCN1C(=O)Cc1ccc(C2CC2)c(F)c1] | 12.5 ± 1.5 |
| 5 | 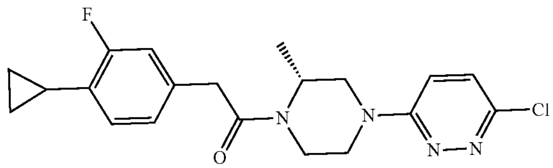 [SMILES: C[C@@H]1CN(c2ccc(Cl)nn2)CCN1C(=O)Cc1ccc(C2CC2)c(F)c1] | 6.9 ± 0.6 |
| 6 | 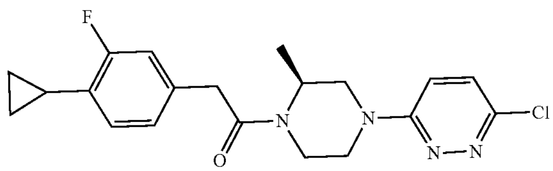 [SMILES: C[C@H]1CN(c2ccc(Cl)nn2)CCN1C(=O)Cc1ccc(C2CC2)c(F)c1] | 2.2 ± 0.3 |
| 7 | 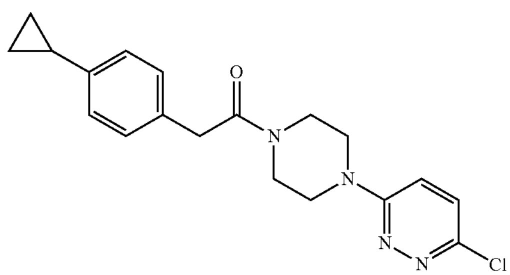 [SMILES: O=C(Cc1ccc(C2CC2)cc1)N1CCN(c2ccc(Cl)nn2)CC1] | 5.8 ± 0.4 |
| 8 | 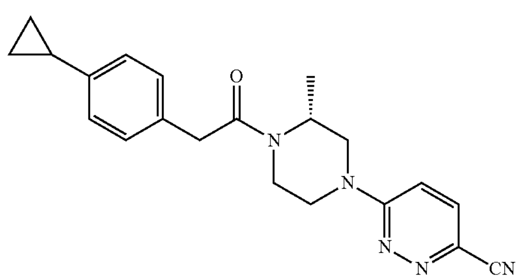 [SMILES: C[C@@H]1CN(c2ccc(C#N)nn2)CCN1C(=O)Cc1ccc(C2CC2)cc1] | 12.9 ± 1.8 |
| 9 | 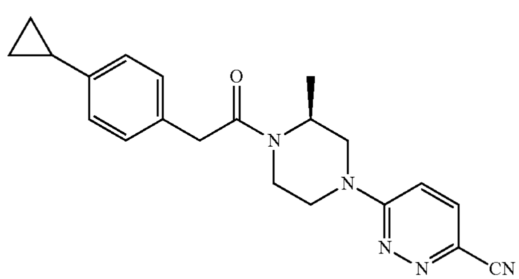 [SMILES: C[C@H]1CN(c2ccc(C#N)nn2)CCN1C(=O)Cc1ccc(C2CC2)cc1] | 5.2 ± 0.6 |

TABLE 1-continued

| No. | Structure | hPanK3 IC$_{50}$ (nM) |
|---|---|---|
| 10 | 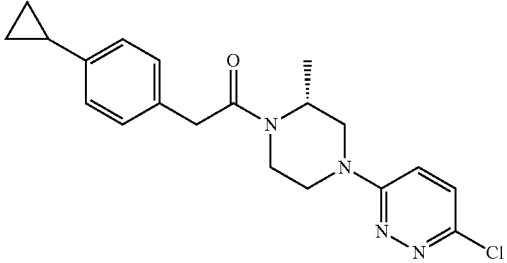 [SMILES: C[C@@H]1CN(c2ccc(Cl)nn2)CCN1C(=O)Cc1ccc(C2CC2)cc1] | 3.8 ± 0.4 |

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound, represented by the formula:

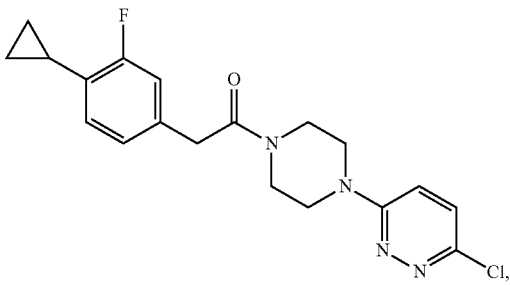 [SMILES: O=C(Cc1ccc(C2CC2)c(F)c1)N1CCN(c2ccc(Cl)nn2)CC1]

or a pharmaceutically acceptable salt thereof.

2. A pharmaceutical composition, comprising a compound, represented by the formula:

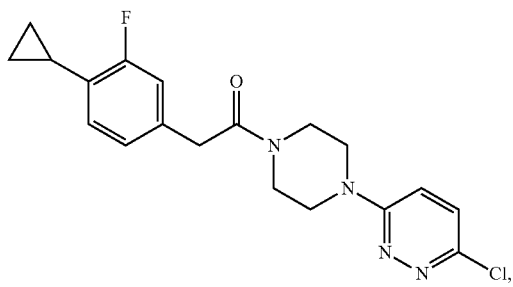 [SMILES: O=C(Cc1ccc(C2CC2)c(F)c1)N1CCN(c2ccc(Cl)nn2)CC1]

or a pharmaceutically acceptable salt thereof, and a pharmaceutically acceptable excipient.

3. The pharmaceutical composition of claim 2, in an oral dosage form.

* * * * *